(12) United States Patent
Sicurello et al.

(10) Patent No.: US 8,509,107 B2
(45) Date of Patent: *Aug. 13, 2013

(54) CLOSE PROXIMITY COMMUNICATION DEVICE AND METHODS

(75) Inventors: Jeffrey Mario Sicurello, Alameda, CA (US); Mark K. Sloan, Redwood City, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 246 days.

This patent is subject to a terminal disclaimer.

(21) Appl. No.: 12/917,455

(22) Filed: Nov. 1, 2010

(65) Prior Publication Data

US 2011/0044333 A1   Feb. 24, 2011

Related U.S. Application Data

(63) Continuation of application No. 12/130,995, filed on May 30, 2008, now Pat. No. 7,826,382.

(51) Int. Cl.
*G08B 1/08* (2006.01)

(52) U.S. Cl.
USPC ...... 370/252; 370/259; 370/310; 340/539.13; 340/572.1; 455/404.1; 600/316; 600/347

(58) Field of Classification Search
None
See application file for complete search history.

(56) References Cited

U.S. PATENT DOCUMENTS

| | | | |
|---|---|---|---|
| 3,581,062 | A | 5/1971 | Aston |
| 3,926,760 | A | 12/1975 | Allen et al. |
| 3,949,388 | A | 4/1976 | Fuller |
| 4,036,749 | A | 7/1977 | Anderson |
| 4,055,175 | A | 10/1977 | Clemens et al. |
| 4,129,128 | A | 12/1978 | McFarlane |
| 4,245,634 | A | 1/1981 | Albisser et al. |
| 4,327,725 | A | 5/1982 | Cortese et al. |
| 4,344,438 | A | 8/1982 | Schultz |
| 4,349,728 | A | 9/1982 | Phillips et al. |
| 4,373,527 | A | 2/1983 | Fischell |
| 4,392,849 | A | 7/1983 | Petre et al. |
| 4,425,920 | A | 1/1984 | Bourland et al. |
| 4,475,901 | A | 10/1984 | Kraegen et al. |
| 4,478,976 | A | 10/1984 | Goertz et al. |
| 4,494,950 | A | 1/1985 | Fischell |

(Continued)

FOREIGN PATENT DOCUMENTS

| | | |
|---|---|---|
| CA | 2143172 | 7/2005 |
| CA | 2605530 | 11/2006 |

(Continued)

OTHER PUBLICATIONS

Isermann, R., "Supervision, Fault-Detection and Fault-Diagnosis Methods—An Introduction", Control Engineering Practice, vol. 5, No. 5, 1997, pp. 639-652.

(Continued)

*Primary Examiner* — Chi Pham
*Assistant Examiner* — Shick Hom
(74) *Attorney, Agent, or Firm* — Jackson & Co., LLP

(57) ABSTRACT

Disclosed herein are methods and systems for receiving an encoded data packet, one or more activation commands, and a communication identifier, decoding the received data packet, validating the decoded received data packet, and executing one or more routines associated with the respective one or more activation commands.

38 Claims, 13 Drawing Sheets

(56) References Cited

U.S. PATENT DOCUMENTS

| | | |
|---|---|---|
| 4,509,531 A | 4/1985 | Ward |
| 4,527,240 A | 7/1985 | Kvitash |
| 4,538,616 A | 9/1985 | Rogoff |
| 4,619,793 A | 10/1986 | Lee |
| 4,671,288 A | 6/1987 | Gough |
| 4,703,324 A | 10/1987 | White |
| 4,703,756 A | 11/1987 | Gough et al. |
| 4,731,726 A | 3/1988 | Allen, III |
| 4,749,985 A | 6/1988 | Corsberg |
| 4,757,022 A | 7/1988 | Shults et al. |
| 4,777,953 A | 10/1988 | Ash et al. |
| 4,779,618 A | 10/1988 | Mund et al. |
| 4,847,785 A | 7/1989 | Stephens |
| 4,854,322 A | 8/1989 | Ash et al. |
| 4,871,351 A | 10/1989 | Feingold |
| 4,890,620 A | 1/1990 | Gough |
| 4,925,268 A | 5/1990 | Iyer et al. |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,051,688 A | 9/1991 | Murase et al. |
| 5,055,171 A | 10/1991 | Peck |
| 5,068,536 A | 11/1991 | Rosenthal |
| 5,082,550 A | 1/1992 | Rishpon et al. |
| 5,106,365 A | 4/1992 | Hernandez |
| 5,122,925 A | 6/1992 | Inpyn |
| 5,135,004 A | 8/1992 | Adams et al. |
| 5,165,407 A | 11/1992 | Wilson et al. |
| 5,245,314 A | 9/1993 | Kah et al. |
| 5,246,867 A | 9/1993 | Lakowicz et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,289,497 A | 2/1994 | Jacokbson et al. |
| 5,293,877 A | 3/1994 | O'Hara et al. |
| 5,299,571 A | 4/1994 | Mastrototaro |
| 5,320,725 A | 6/1994 | Gregg et al. |
| 5,322,063 A | 6/1994 | Allen et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,372,427 A | 12/1994 | Padovani et al. |
| 5,379,238 A | 1/1995 | Stark |
| 5,390,671 A | 2/1995 | Lord et al. |
| 5,391,250 A | 2/1995 | Cheney, II et al. |
| 5,400,794 A | 3/1995 | Gorman |
| 5,408,999 A | 4/1995 | Singh et al. |
| 5,410,326 A | 4/1995 | Goldstein |
| 5,411,647 A | 5/1995 | Johnson et al. |
| 5,425,868 A | 6/1995 | Pedersen |
| 5,431,160 A | 7/1995 | Wilkins |
| 5,431,921 A | 7/1995 | Thombre |
| 5,462,051 A | 10/1995 | Oka et al. |
| 5,462,645 A | 10/1995 | Albery et al. |
| 5,497,772 A | 3/1996 | Schulman et al. |
| 5,499,243 A | 3/1996 | Hall |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,532,686 A | 7/1996 | Urbas et al. |
| 5,544,196 A | 8/1996 | Tiedemann, Jr. et al. |
| 5,568,806 A | 10/1996 | Cheney, II et al. |
| 5,569,186 A | 10/1996 | Lord et al. |
| 5,581,206 A | 12/1996 | Chevallier et al. |
| 5,582,184 A | 12/1996 | Erickson et al. |
| 5,586,553 A | 12/1996 | Halili et al. |
| 5,593,852 A | 1/1997 | Heller et al. |
| 5,600,301 A | 2/1997 | Robinson, III |
| 5,609,575 A | 3/1997 | Larson et al. |
| 5,628,310 A | 5/1997 | Rao et al. |
| 5,634,468 A | 6/1997 | Platt et al. |
| 5,653,239 A | 8/1997 | Pompei et al. |
| 5,659,454 A | 8/1997 | Vermesse |
| 5,665,222 A | 9/1997 | Heller et al. |
| 5,707,502 A | 1/1998 | McCaffrey et al. |
| 5,711,001 A | 1/1998 | Bussan et al. |
| 5,711,861 A | 1/1998 | Ward et al. |
| 5,724,030 A | 3/1998 | Urbas et al. |
| 5,733,259 A | 3/1998 | Valcke et al. |
| 5,748,103 A | 5/1998 | Flach et al. |
| 5,749,907 A | 5/1998 | Mann |
| 5,758,290 A | 5/1998 | Nealon et al. |
| 5,772,586 A | 6/1998 | Heinonen et al. |
| 5,791,344 A | 8/1998 | Schulman et al. |
| 5,804,047 A | 9/1998 | Karube et al. |
| 5,833,603 A | 11/1998 | Kovacs et al. |
| 5,891,049 A | 4/1999 | Cyrus et al. |
| 5,899,855 A | 5/1999 | Brown |
| 5,925,021 A | 7/1999 | Castellano et al. |
| 5,935,099 A | 8/1999 | Petterson |
| 5,935,224 A | 8/1999 | Svancarek et al. |
| 5,942,979 A | 8/1999 | Luppino |
| 5,951,485 A | 9/1999 | Cyrus et al. |
| 5,957,854 A | 9/1999 | Besson et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,995,860 A | 11/1999 | Sun et al. |
| 6,001,067 A | 12/1999 | Shults et al. |
| 6,024,699 A | 2/2000 | Surwit et al. |
| 6,049,727 A | 4/2000 | Crothall |
| 6,052,565 A | 4/2000 | Ishikura et al. |
| 6,066,243 A | 5/2000 | Anderson et al. |
| 6,083,710 A | 7/2000 | Heller et al. |
| 6,088,608 A | 7/2000 | Schulman et al. |
| 6,091,976 A | 7/2000 | Pfeiffer et al. |
| 6,091,987 A | 7/2000 | Thompson |
| 6,093,172 A | 7/2000 | Funderburk et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,130,623 A | 10/2000 | MacLellan et al. |
| 6,134,461 A | 10/2000 | Say et al. |
| 6,144,871 A | 11/2000 | Saito et al. |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,233,471 B1 | 5/2001 | Berner et al. |
| 6,248,067 B1 | 6/2001 | Causey, III et al. |
| 6,275,717 B1 | 8/2001 | Gross et al. |
| 6,284,478 B1 | 9/2001 | Heller et al. |
| 6,291,200 B1 | 9/2001 | LeJeune et al. |
| 6,293,925 B1 | 9/2001 | Safabash et al. |
| 6,294,997 B1 | 9/2001 | Paratore et al. |
| 6,295,506 B1 | 9/2001 | Heinonen et al. |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,359,270 B1 * | 3/2002 | Bridson .................. 219/679 |
| 6,360,888 B1 | 3/2002 | McIvor et al. |
| 6,366,794 B1 | 4/2002 | Moussy et al. |
| 6,377,828 B1 | 4/2002 | Chaiken et al. |
| 6,379,301 B1 | 4/2002 | Worthington et al. |
| 6,387,048 B1 | 5/2002 | Schulman et al. |
| 6,400,974 B1 | 6/2002 | Lesho |
| 6,405,066 B1 | 6/2002 | Essenpreis et al. |
| 6,413,393 B1 | 7/2002 | Van Antwerp et al. |
| 6,416,471 B1 | 7/2002 | Kumar et al. |
| 6,418,346 B1 | 7/2002 | Nelson et al. |

| Patent | Date | Inventor |
|---|---|---|
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,442,672 B1 | 8/2002 | Ganapathy |
| 6,478,736 B1 | 11/2002 | Mault |
| 6,484,046 B1 | 11/2002 | Say et al. |
| 6,496,729 B2 | 12/2002 | Thompson |
| 6,497,655 B1 | 12/2002 | Linberg et al. |
| 6,514,718 B2 | 2/2003 | Heller et al. |
| 6,520,326 B2 | 2/2003 | McIvor et al. |
| 6,544,212 B2 | 4/2003 | Galley et al. |
| 6,549,796 B2 | 4/2003 | Sohrab |
| 6,551,494 B1 | 4/2003 | Heller et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,975 B1 | 5/2003 | Pool et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,574,510 B2 | 6/2003 | Von Arx et al. |
| 6,576,101 B1 | 6/2003 | Heller et al. |
| 6,577,899 B2 | 6/2003 | Lebel et al. |
| 6,579,231 B1 | 6/2003 | Phipps |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,611,206 B2 | 8/2003 | Eshelman et al. |
| 6,627,154 B1 | 9/2003 | Goodman et al. |
| 6,633,772 B2 | 10/2003 | Ford et al. |
| 6,635,014 B2 | 10/2003 | Starkweather et al. |
| 6,635,167 B1 | 10/2003 | Batman et al. |
| 6,641,533 B2 | 11/2003 | Causey, III et al. |
| 6,648,821 B2 | 11/2003 | Lebel et al. |
| 6,654,625 B1 | 11/2003 | Say et al. |
| 6,659,948 B2 | 12/2003 | Lebel et al. |
| 6,668,196 B1 | 12/2003 | Villegas et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,731,976 B2 | 5/2004 | Penn et al. |
| 6,733,446 B2 | 5/2004 | Lebel et al. |
| 6,735,183 B2 | 5/2004 | O'Toole et al. |
| 6,735,479 B2 | 5/2004 | Fabian et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,758,810 B2 | 7/2004 | Lebel et al. |
| 6,770,030 B1 | 8/2004 | Schaupp et al. |
| 6,790,178 B1 | 9/2004 | Mault et al. |
| 6,804,558 B2 | 10/2004 | Haller et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,850,790 B2 | 2/2005 | Berner et al. |
| 6,862,465 B2 | 3/2005 | Shults et al. |
| 6,873,268 B2 | 3/2005 | Lebel et al. |
| 6,878,112 B2 | 4/2005 | Linberg et al. |
| 6,881,551 B2 | 4/2005 | Heller et al. |
| 6,889,331 B2 | 5/2005 | Soerensen et al. |
| 6,892,085 B2 | 5/2005 | McIvor et al. |
| 6,895,263 B2 | 5/2005 | Shin et al. |
| 6,895,265 B2 | 5/2005 | Silver |
| 6,923,764 B2 | 8/2005 | Aceti et al. |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,937,222 B2 | 8/2005 | Numao |
| 6,940,403 B2 | 9/2005 | Kail, IV |
| 6,941,163 B2 | 9/2005 | Ford et al. |
| 6,950,708 B2 | 9/2005 | Bowman, IV et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,009,511 B2 | 3/2006 | Mazar et al. |
| 7,020,508 B2 | 3/2006 | Stivoric et al. |
| 7,022,072 B2 | 4/2006 | Fox et al. |
| 7,024,236 B2 | 4/2006 | Ford et al. |
| 7,024,245 B2 | 4/2006 | Lebel et al. |
| 7,029,444 B2 | 4/2006 | Shin et al. |
| 7,041,068 B2 | 5/2006 | Freeman et al. |
| 7,043,305 B2 | 5/2006 | KenKnight et al. |
| 7,052,483 B2 | 5/2006 | Wojcik |
| 7,056,302 B2 | 6/2006 | Douglas |
| 7,058,453 B2 | 6/2006 | Nelson et al. |
| 7,060,031 B2 | 6/2006 | Webb et al. |
| 7,074,307 B2 | 7/2006 | Simpson et al. |
| 7,081,195 B2 | 7/2006 | Simpson et al. |
| 7,082,334 B2 | 7/2006 | Boute et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,124,027 B1 | 10/2006 | Ernst et al. |
| 7,125,382 B2 | 10/2006 | Zhou et al. |
| 7,134,999 B2 | 11/2006 | Brauker et al. |
| 7,136,689 B2 | 11/2006 | Shults et al. |
| 7,154,398 B2 | 12/2006 | Chen et al. |
| 7,155,290 B2 | 12/2006 | Von Arx et al. |
| 7,171,274 B2 | 1/2007 | Starkweather et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,203,549 B2 | 4/2007 | Schommer et al. |
| 7,207,974 B2 | 4/2007 | Safabash et al. |
| 7,225,535 B2 | 6/2007 | Feldman et al. |
| 7,226,442 B2 | 6/2007 | Sheppard et al. |
| 7,226,978 B2 | 6/2007 | Tapsak et al. |
| 7,228,162 B2 | 6/2007 | Ward et al. |
| 7,228,182 B2 | 6/2007 | Healy et al. |
| 7,237,712 B2 | 7/2007 | DeRocco et al. |
| 7,267,665 B2 | 9/2007 | Steil et al. |
| 7,276,029 B2 | 10/2007 | Goode, Jr. et al. |
| 7,286,894 B1 | 10/2007 | Grant et al. |
| 7,295,867 B2 | 11/2007 | Berner et al. |
| 7,299,082 B2 | 11/2007 | Feldman et al. |
| 7,310,544 B2 | 12/2007 | Brister et al. |
| 7,318,816 B2 | 1/2008 | Bobroff et al. |
| 7,324,850 B2 | 1/2008 | Persen et al. |
| 7,335,294 B2 | 2/2008 | Heller et al. |
| 7,347,819 B2 | 3/2008 | Lebel et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,384,397 B2 | 6/2008 | Zhang et al. |
| 7,387,010 B2 | 6/2008 | Sunshine et al. |
| 7,399,277 B2 | 7/2008 | Saidara et al. |
| 7,402,153 B2 | 7/2008 | Steil et al. |
| 7,408,132 B2 | 8/2008 | Wambsganss et al. |
| 7,419,573 B2 | 9/2008 | Gundel |
| 7,424,318 B2 | 9/2008 | Brister et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,492,254 B2 | 2/2009 | Bandy et al. |
| 7,494,465 B2 | 2/2009 | Brister et al. |

| | | | |
|---|---|---|---|
| 7,497,827 B2 | 3/2009 | Brister et al. | |
| 7,519,408 B2 | 4/2009 | Rasdal et al. | |
| 7,547,281 B2 | 6/2009 | Hayes et al. | |
| 7,565,197 B2 | 7/2009 | Haubrich et al. | |
| 7,569,030 B2 | 8/2009 | Lebel et al. | |
| 7,574,266 B2 | 8/2009 | Dudding et al. | |
| 7,583,990 B2 | 9/2009 | Goode, Jr. et al. | |
| 7,591,801 B2 | 9/2009 | Brauker et al. | |
| 7,599,726 B2 | 10/2009 | Goode, Jr. et al. | |
| 7,602,310 B2 | 10/2009 | Mann et al. | |
| 7,604,178 B2 | 10/2009 | Stewart | |
| 7,613,491 B2 | 11/2009 | Boock et al. | |
| 7,615,007 B2 | 11/2009 | Shults et al. | |
| 7,618,369 B2 | 11/2009 | Hayter et al. | |
| 7,632,228 B2 | 12/2009 | Brauker et al. | |
| 7,637,868 B2 | 12/2009 | Saint et al. | |
| 7,640,048 B2 | 12/2009 | Dobbles et al. | |
| 7,651,596 B2 | 1/2010 | Petisce et al. | |
| 7,654,956 B2 | 2/2010 | Brister et al. | |
| 7,657,297 B2 | 2/2010 | Simpson et al. | |
| 7,659,823 B1 | 2/2010 | Killian et al. | |
| 7,668,596 B2 | 2/2010 | Von Arx et al. | |
| 7,699,775 B2 | 4/2010 | Desai et al. | |
| 7,701,052 B2 | 4/2010 | Borland et al. | |
| 7,711,402 B2 | 5/2010 | Shults et al. | |
| 7,713,574 B2 | 5/2010 | Brister et al. | |
| 7,715,893 B2 | 5/2010 | Kamath et al. | |
| 7,741,734 B2 | 6/2010 | Joannopoulos et al. | |
| 7,771,352 B2 | 8/2010 | Shults et al. | |
| 7,774,145 B2 | 8/2010 | Brauker et al. | |
| 7,779,332 B2 | 8/2010 | Karr et al. | |
| 7,782,192 B2 | 8/2010 | Jeckelmann et al. | |
| 7,783,333 B2 | 8/2010 | Brister et al. | |
| 7,791,467 B2 | 9/2010 | Mazar et al. | |
| 7,792,562 B2 | 9/2010 | Shults et al. | |
| 7,813,809 B2 | 10/2010 | Strother et al. | |
| 7,826,382 B2 * | 11/2010 | Sicurello et al. | 370/242 |
| 7,826,981 B2 | 11/2010 | Goode, Jr. et al. | |
| 7,831,310 B2 | 11/2010 | Lebel et al. | |
| 7,860,574 B2 | 12/2010 | Von Arx et al. | |
| 7,882,611 B2 | 2/2011 | Shah et al. | |
| 7,899,511 B2 | 3/2011 | Shults et al. | |
| 7,905,833 B2 | 3/2011 | Brister et al. | |
| 7,912,674 B2 | 3/2011 | Clark et al. | |
| 7,914,450 B2 | 3/2011 | Goode, Jr. et al. | |
| 7,916,013 B2 | 3/2011 | Stevenson | |
| 7,948,369 B2 | 5/2011 | Fennell et al. | |
| 7,955,258 B2 | 6/2011 | Goscha et al. | |
| 7,970,448 B2 | 6/2011 | Shults et al. | |
| 7,974,672 B2 | 7/2011 | Shults et al. | |
| 7,978,063 B2 | 7/2011 | Baldus et al. | |
| 7,999,674 B2 | 8/2011 | Kamen | |
| 8,072,310 B1 | 12/2011 | Everhart | |
| 8,090,445 B2 | 1/2012 | Ginggen | |
| 8,093,991 B2 | 1/2012 | Stevenson et al. | |
| 8,094,009 B2 | 1/2012 | Allen et al. | |
| 8,098,159 B2 | 1/2012 | Batra et al. | |
| 8,098,160 B2 | 1/2012 | Howarth et al. | |
| 8,098,161 B2 | 1/2012 | Lavedas | |
| 8,098,201 B2 | 1/2012 | Choi et al. | |
| 8,098,208 B2 | 1/2012 | Ficker et al. | |
| 8,102,021 B2 | 1/2012 | Degani | |
| 8,102,154 B2 | 1/2012 | Bishop et al. | |
| 8,102,263 B2 | 1/2012 | Yeo et al. | |
| 8,102,789 B2 | 1/2012 | Rosar et al. | |
| 8,103,241 B2 | 1/2012 | Young et al. | |
| 8,103,325 B2 | 1/2012 | Swedlow et al. | |
| 8,111,042 B2 | 2/2012 | Bennett | |
| 8,115,488 B2 | 2/2012 | McDowell | |
| 8,116,681 B2 | 2/2012 | Baarman | |
| 8,116,683 B2 | 2/2012 | Baarman | |
| 8,117,481 B2 | 2/2012 | Anselmi et al. | |
| 8,120,493 B2 | 2/2012 | Burr | |
| 8,124,452 B2 | 2/2012 | Sheats | |
| 8,130,093 B2 | 3/2012 | Mazar et al. | |
| 8,131,351 B2 | 3/2012 | Kalgren et al. | |
| 8,131,365 B2 | 3/2012 | Zhang et al. | |
| 8,131,565 B2 | 3/2012 | Dicks et al. | |
| 8,132,037 B2 | 3/2012 | Fehr et al. | |
| 8,135,352 B2 | 3/2012 | Langsweirdt et al. |
| 8,136,735 B2 | 3/2012 | Arai et al. |
| 8,138,925 B2 | 3/2012 | Downie et al. |
| 8,140,160 B2 | 3/2012 | Pless et al. |
| 8,140,168 B2 | 3/2012 | Olson et al. |
| 8,140,299 B2 | 3/2012 | Siess |
| 8,150,321 B2 | 4/2012 | Winter et al. |
| 8,150,516 B2 | 4/2012 | Levine et al. |
| 8,179,266 B2 | 5/2012 | Hermle |
| 2001/0037366 A1 | 11/2001 | Webb et al. |
| 2001/0047127 A1 | 11/2001 | New et al. |
| 2002/0013522 A1 | 1/2002 | Lav et al. |
| 2002/0013538 A1 | 1/2002 | Teller |
| 2002/0019022 A1 | 2/2002 | Dunn et al. |
| 2002/0019584 A1 | 2/2002 | Schulze et al. |
| 2002/0042090 A1 | 4/2002 | Heller et al. |
| 2002/0049482 A1 | 4/2002 | Fabian et al. |
| 2002/0072784 A1 | 6/2002 | Sheppard et al. |
| 2002/0074162 A1 | 6/2002 | Su et al. |
| 2002/0084196 A1 | 7/2002 | Liamos et al. |
| 2002/0091796 A1 | 7/2002 | Higginson et al. |
| 2002/0093969 A1 | 7/2002 | Lin et al. |
| 2002/0103499 A1 | 8/2002 | Perez et al. |
| 2002/0106709 A1 | 8/2002 | Potts et al. |
| 2002/0118528 A1 | 8/2002 | Su et al. |
| 2002/0128594 A1 | 9/2002 | Das et al. |
| 2002/0161288 A1 | 10/2002 | Shin et al. |
| 2002/0169635 A1 | 11/2002 | Shillingburg |
| 2003/0004403 A1 | 1/2003 | Drinan et al. |
| 2003/0023317 A1 | 1/2003 | Brauker et al. |
| 2003/0032874 A1 | 2/2003 | Rhodes et al. |
| 2003/0042137 A1 | 3/2003 | Mao et al. |
| 2003/0065308 A1 | 4/2003 | Lebel et al. |
| 2003/0076792 A1 | 4/2003 | Theimer |
| 2003/0100821 A1 | 5/2003 | Heller et al. |
| 2003/0114897 A1 | 6/2003 | Von Arx et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0144579 A1 | 7/2003 | Buss |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0199790 A1 | 10/2003 | Boecker et al. |
| 2003/0204290 A1 | 10/2003 | Sadler et al. |
| 2003/0208113 A1 | 11/2003 | Mault et al. |
| 2003/0208114 A1 | 11/2003 | Ackerman |
| 2003/0212317 A1 | 11/2003 | Kovatchev et al. |
| 2003/0212379 A1 | 11/2003 | Bylund et al. |
| 2003/0212579 A1 | 11/2003 | Brown et al. |
| 2003/0216630 A1 | 11/2003 | Jersey-Willuhn et al. |
| 2003/0217966 A1 | 11/2003 | Tapsak et al. |
| 2004/0010207 A1 | 1/2004 | Flaherty et al. |
| 2004/0011671 A1 | 1/2004 | Shults et al. |
| 2004/0017300 A1 | 1/2004 | Kotzin et al. |
| 2004/0030531 A1 | 2/2004 | Miller et al. |
| 2004/0039298 A1 | 2/2004 | Abreu |
| 2004/0040840 A1 | 3/2004 | Mao et al. |
| 2004/0041749 A1 | 3/2004 | Dixon |
| 2004/0045879 A1 | 3/2004 | Shults et al. |
| 2004/0064068 A1 | 4/2004 | DeNuzzio et al. |
| 2004/0100376 A1 | 5/2004 | Lye et al. |
| 2004/0105411 A1 | 6/2004 | Boatwright et al. |
| 2004/0106858 A1 | 6/2004 | Say et al. |
| 2004/0122353 A1 | 6/2004 | Shahmirian et al. |
| 2004/0133164 A1 | 7/2004 | Funderburk et al. |
| 2004/0138588 A1 | 7/2004 | Saikley et al. |
| 2004/0146909 A1 | 7/2004 | Duong et al. |
| 2004/0152622 A1 | 8/2004 | Keith et al. |
| 2004/0167801 A1 | 8/2004 | Say et al. |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199059 A1 | 10/2004 | Brauker et al. |
| 2004/0204687 A1 | 10/2004 | Mogensen et al. |

| | | | | | | |
|---|---|---|---|---|---|---|
| 2004/0225338 A1 | 11/2004 | Lebel et al. | | 2006/0272652 A1 | 12/2006 | Stocker et al. |
| 2004/0236200 A1 | 11/2004 | Say et al. | | 2006/0287691 A1 | 12/2006 | Drew |
| 2004/0254433 A1 | 12/2004 | Bandis et al. | | 2006/0290496 A1 | 12/2006 | Peeters et al. |
| 2004/0267300 A1 | 12/2004 | Mace | | 2006/0293607 A1 | 12/2006 | Alt et al. |
| 2005/0004439 A1 | 1/2005 | Shin et al. | | 2007/0016381 A1 | 1/2007 | Kamath et al. |
| 2005/0004494 A1 | 1/2005 | Perez et al. | | 2007/0027381 A1 | 2/2007 | Stafford |
| 2005/0010269 A1 | 1/2005 | Lebel et al. | | 2007/0033074 A1 | 2/2007 | Nitzan et al. |
| 2005/0027177 A1 | 2/2005 | Shin et al. | | 2007/0055799 A1 | 3/2007 | Koehler et al. |
| 2005/0031689 A1 | 2/2005 | Shults et al. | | 2007/0060814 A1 | 3/2007 | Stafford |
| 2005/0038332 A1 | 2/2005 | Saidara et al. | | 2007/0066873 A1 | 3/2007 | Kamath et al. |
| 2005/0043598 A1 | 2/2005 | Goode, Jr. et al. | | 2007/0071681 A1 | 3/2007 | Gadkar et al. |
| 2005/0090607 A1 | 4/2005 | Tapsak et al. | | 2007/0073129 A1 | 3/2007 | Shah et al. |
| 2005/0096511 A1 | 5/2005 | Fox et al. | | 2007/0078320 A1 | 4/2007 | Stafford |
| 2005/0096512 A1 | 5/2005 | Fox et al. | | 2007/0078321 A1 | 4/2007 | Mazza et al. |
| 2005/0112169 A1 | 5/2005 | Brauker et al. | | 2007/0078322 A1 | 4/2007 | Stafford |
| 2005/0113653 A1 | 5/2005 | Fox et al. | | 2007/0078323 A1 | 4/2007 | Reggiardo et al. |
| 2005/0113886 A1 | 5/2005 | Fischell et al. | | 2007/0106135 A1 | 5/2007 | Sloan et al. |
| 2005/0114068 A1 | 5/2005 | Chey et al. | | 2007/0124002 A1 | 5/2007 | Estes et al. |
| 2005/0121322 A1 | 6/2005 | Say et al. | | 2007/0149875 A1 | 6/2007 | Ouyang et al. |
| 2005/0131346 A1 | 6/2005 | Douglas | | 2007/0156033 A1 | 7/2007 | Causey, III et al. |
| 2005/0143635 A1 | 6/2005 | Kamath et al. | | 2007/0163880 A1 | 7/2007 | Woo et al. |
| 2005/0176136 A1 | 8/2005 | Burd et al. | | 2007/0168224 A1 | 7/2007 | Letzt et al. |
| 2005/0177398 A1 | 8/2005 | Watanabe et al. | | 2007/0173706 A1 | 7/2007 | Neinast et al. |
| 2005/0182306 A1 | 8/2005 | Sloan | | 2007/0173761 A1 | 7/2007 | Kanderian et al. |
| 2005/0187720 A1 | 8/2005 | Goode, Jr. et al. | | 2007/0179349 A1 | 8/2007 | Hoyme et al. |
| 2005/0192494 A1 | 9/2005 | Ginsberg | | 2007/0179352 A1 | 8/2007 | Randlov et al. |
| 2005/0192557 A1 | 9/2005 | Brauker et al. | | 2007/0191701 A1 | 8/2007 | Feldman et al. |
| 2005/0195930 A1 | 9/2005 | Spital et al. | | 2007/0203407 A1 | 8/2007 | Hoss et al. |
| 2005/0199494 A1 | 9/2005 | Say et al. | | 2007/0203966 A1 | 8/2007 | Brauker et al. |
| 2005/0203360 A1 | 9/2005 | Brauker et al. | | 2007/0232880 A1 | 10/2007 | Siddiqui et al. |
| 2005/0204134 A1 | 9/2005 | Von Arx et al. | | 2007/0235331 A1 | 10/2007 | Simpson et al. |
| 2005/0239154 A1 | 10/2005 | Feldman et al. | | 2007/0244383 A1 | 10/2007 | Talbot et al. |
| 2005/0241957 A1 | 11/2005 | Mao et al. | | 2007/0249922 A1 | 10/2007 | Peyser et al. |
| 2005/0245795 A1 | 11/2005 | Goode, Jr. et al. | | 2007/0253021 A1 | 11/2007 | Mehta et al. |
| 2005/0245799 A1 | 11/2005 | Brauker et al. | | 2007/0255348 A1 | 11/2007 | Holtzclaw |
| 2005/0245839 A1 | 11/2005 | Stivoric et al. | | 2007/0255531 A1 | 11/2007 | Drew |
| 2005/0245904 A1 | 11/2005 | Estes et al. | | 2007/0258395 A1 | 11/2007 | Jollota et al. |
| 2005/0251033 A1 | 11/2005 | Scarantino et al. | | 2007/0270672 A1 | 11/2007 | Hayter |
| 2005/0287620 A1 | 12/2005 | Heller et al. | | 2007/0285238 A1 | 12/2007 | Batra |
| 2006/0001538 A1 | 1/2006 | Kraft et al. | | 2008/0009304 A1 | 1/2008 | Fry |
| 2006/0004270 A1 | 1/2006 | Bedard et al. | | 2008/0009692 A1 | 1/2008 | Stafford |
| 2006/0015020 A1 | 1/2006 | Neale et al. | | 2008/0017522 A1 | 1/2008 | Heller et al. |
| 2006/0015024 A1 | 1/2006 | Brister et al. | | 2008/0018433 A1 | 1/2008 | Pitt-Pladdy |
| 2006/0016700 A1 | 1/2006 | Brister et al. | | 2008/0021666 A1 | 1/2008 | Goode, Jr. et al. |
| 2006/0019327 A1 | 1/2006 | Brister et al. | | 2008/0029391 A1 | 2/2008 | Mao et al. |
| 2006/0020186 A1 | 1/2006 | Brister et al. | | 2008/0030369 A1 | 2/2008 | Mann et al. |
| 2006/0020187 A1 | 1/2006 | Brister et al. | | 2008/0033254 A1 | 2/2008 | Kamath et al. |
| 2006/0020188 A1 | 1/2006 | Kamath et al. | | 2008/0039702 A1 | 2/2008 | Hayter et al. |
| 2006/0020189 A1 | 1/2006 | Brister et al. | | 2008/0045161 A1 | 2/2008 | Lee et al. |
| 2006/0020190 A1 | 1/2006 | Kamath et al. | | 2008/0045824 A1 | 2/2008 | Tapsak et al. |
| 2006/0020191 A1 | 1/2006 | Brister et al. | | 2008/0055070 A1 | 3/2008 | Bange et al. |
| 2006/0020192 A1 | 1/2006 | Brister et al. | | 2008/0058625 A1 | 3/2008 | McGarraugh et al. |
| 2006/0029177 A1 | 2/2006 | Cranford, Jr. et al. | | 2008/0060955 A1 | 3/2008 | Goodnow |
| 2006/0031094 A1 | 2/2006 | Cohen et al. | | 2008/0064937 A1 | 3/2008 | McGarraugh et al. |
| 2006/0036139 A1 | 2/2006 | Brister et al. | | 2008/0064943 A1 | 3/2008 | Talbot et al. |
| 2006/0036140 A1 | 2/2006 | Brister et al. | | 2008/0071156 A1 | 3/2008 | Brister et al. |
| 2006/0036141 A1 | 2/2006 | Kamath et al. | | 2008/0071157 A1 | 3/2008 | McGarraugh et al. |
| 2006/0036142 A1 | 2/2006 | Brister et al. | | 2008/0071158 A1 | 3/2008 | McGarraugh et al. |
| 2006/0036143 A1 | 2/2006 | Brister et al. | | 2008/0071328 A1 | 3/2008 | Haubrich et al. |
| 2006/0036144 A1 | 2/2006 | Brister et al. | | 2008/0081977 A1 | 4/2008 | Hayter et al. |
| 2006/0036145 A1 | 2/2006 | Brister et al. | | 2008/0083617 A1 | 4/2008 | Simpson et al. |
| 2006/0129733 A1 | 6/2006 | Sobelman | | 2008/0086042 A1 | 4/2008 | Brister et al. |
| 2006/0142651 A1 | 6/2006 | Brister et al. | | 2008/0086044 A1 | 4/2008 | Brister et al. |
| 2006/0154642 A1* | 7/2006 | Scannell, Jr. ............... 455/404.1 | | 2008/0086273 A1 | 4/2008 | Shults et al. |
| 2006/0155180 A1 | 7/2006 | Brister et al. | | 2008/0097289 A1 | 4/2008 | Steil et al. |
| 2006/0166629 A1 | 7/2006 | Reggiardo | | 2008/0108942 A1 | 5/2008 | Brister et al. |
| 2006/0173260 A1 | 8/2006 | Gaoni et al. | | 2008/0119705 A1 | 5/2008 | Patel et al. |
| 2006/0173406 A1 | 8/2006 | Hayes et al. | | 2008/0139910 A1 | 6/2008 | Mastrototaro et al. |
| 2006/0173444 A1 | 8/2006 | Choy et al. | | 2008/0154513 A1 | 6/2008 | Kovatchev et al. |
| 2006/0183985 A1 | 8/2006 | Brister et al. | | 2008/0167543 A1 | 7/2008 | Say et al. |
| 2006/0189863 A1 | 8/2006 | Peyser et al. | | 2008/0167572 A1 | 7/2008 | Stivoric et al. |
| 2006/0202805 A1 | 9/2006 | Schulman et al. | | 2008/0172205 A1 | 7/2008 | Breton et al. |
| 2006/0202859 A1 | 9/2006 | Mastrototaro et al. | | 2008/0183060 A1 | 7/2008 | Steil et al. |
| 2006/0222566 A1 | 10/2006 | Brauker et al. | | 2008/0183061 A1 | 7/2008 | Goode et al. |
| 2006/0224109 A1 | 10/2006 | Steil et al. | | 2008/0183399 A1 | 7/2008 | Goode et al. |
| 2006/0224141 A1 | 10/2006 | Rush et al. | | 2008/0188731 A1 | 8/2008 | Brister et al. |
| 2006/0229512 A1 | 10/2006 | Petisce et al. | | 2008/0188796 A1 | 8/2008 | Steil et al. |
| 2006/0247508 A1 | 11/2006 | Fennell | | 2008/0189051 A1 | 8/2008 | Goode et al. |
| 2006/0247710 A1 | 11/2006 | Goetz et al. | | 2008/0194934 A1 | 8/2008 | Ray et al. |

| | | | | | | |
|---|---|---|---|---|---|---|
| 2008/0194935 A1 | 8/2008 | Brister et al. | | 2009/0105554 A1 | 4/2009 | Stahmann et al. |
| 2008/0194936 A1 | 8/2008 | Goode et al. | | 2009/0105636 A1 | 4/2009 | Hayter et al. |
| 2008/0194937 A1 | 8/2008 | Goode et al. | | 2009/0112478 A1 | 4/2009 | Mueller, Jr. et al. |
| 2008/0194938 A1 | 8/2008 | Brister et al. | | 2009/0124877 A1 | 5/2009 | Goode et al. |
| 2008/0195232 A1 | 8/2008 | Carr-Brendel et al. | | 2009/0124878 A1 | 5/2009 | Goode et al. |
| 2008/0195967 A1 | 8/2008 | Goode et al. | | 2009/0124879 A1 | 5/2009 | Brister et al. |
| 2008/0197024 A1 | 8/2008 | Simpson et al. | | 2009/0124964 A1 | 5/2009 | Leach et al. |
| 2008/0200788 A1 | 8/2008 | Brister et al. | | 2009/0131768 A1 | 5/2009 | Simpson et al. |
| 2008/0200789 A1 | 8/2008 | Brister et al. | | 2009/0131769 A1 | 5/2009 | Leach et al. |
| 2008/0200791 A1 | 8/2008 | Simpson et al. | | 2009/0131776 A1 | 5/2009 | Simpson et al. |
| 2008/0208025 A1 | 8/2008 | Shults et al. | | 2009/0131777 A1 | 5/2009 | Simpson et al. |
| 2008/0208113 A1 | 8/2008 | Damiano et al. | | 2009/0137886 A1 | 5/2009 | Shariati et al. |
| 2008/0214915 A1 | 9/2008 | Brister et al. | | 2009/0137887 A1 | 5/2009 | Shariati et al. |
| 2008/0214918 A1 | 9/2008 | Brister et al. | | 2009/0143659 A1 | 6/2009 | Li et al. |
| 2008/0228051 A1 | 9/2008 | Shults et al. | | 2009/0143660 A1 | 6/2009 | Brister et al. |
| 2008/0228054 A1 | 9/2008 | Shults et al. | | 2009/0150186 A1 | 6/2009 | Cohen et al. |
| 2008/0235469 A1 | 9/2008 | Drew | | 2009/0156919 A1 | 6/2009 | Brister et al. |
| 2008/0242961 A1 | 10/2008 | Brister et al. | | 2009/0156924 A1 | 6/2009 | Shariati et al. |
| 2008/0255434 A1 | 10/2008 | Hayter et al. | | 2009/0163790 A1 | 6/2009 | Brister et al. |
| 2008/0255437 A1 | 10/2008 | Hayter | | 2009/0163791 A1 | 6/2009 | Brister et al. |
| 2008/0255438 A1 | 10/2008 | Saidara et al. | | 2009/0164190 A1 | 6/2009 | Hayter |
| 2008/0255808 A1 | 10/2008 | Hayter | | 2009/0164239 A1 | 6/2009 | Hayter et al. |
| 2008/0256048 A1 | 10/2008 | Hayter | | 2009/0164251 A1 | 6/2009 | Hayter |
| 2008/0262469 A1 | 10/2008 | Brister et al. | | 2009/0178459 A1 | 7/2009 | Li et al. |
| 2008/0275313 A1 | 11/2008 | Brister et al. | | 2009/0182217 A1 | 7/2009 | Li et al. |
| 2008/0278331 A1 | 11/2008 | Hayter et al. | | 2009/0189738 A1 | 7/2009 | Hermle |
| 2008/0278332 A1 | 11/2008 | Fennell et al. | | 2009/0192366 A1 | 7/2009 | Mensinger et al. |
| 2008/0278333 A1 | 11/2008 | Fennell et al. | | 2009/0192380 A1 | 7/2009 | Shariati et al. |
| 2008/0281171 A1 | 11/2008 | Fennell et al. | | 2009/0192722 A1 | 7/2009 | Shariati et al. |
| 2008/0281179 A1 | 11/2008 | Fennell et al. | | 2009/0192724 A1 | 7/2009 | Brauker et al. |
| 2008/0281840 A1 | 11/2008 | Fennell et al. | | 2009/0192745 A1 | 7/2009 | Kamath et al. |
| 2008/0287761 A1 | 11/2008 | Hayter | | 2009/0192751 A1 | 7/2009 | Kamath et al. |
| 2008/0287762 A1 | 11/2008 | Hayter | | 2009/0198118 A1 | 8/2009 | Hayter et al. |
| 2008/0287763 A1 | 11/2008 | Hayter | | 2009/0203981 A1 | 8/2009 | Brauker et al. |
| 2008/0287764 A1 | 11/2008 | Rasdal et al. | | 2009/0204341 A1 | 8/2009 | Brauker et al. |
| 2008/0287765 A1 | 11/2008 | Rasdal et al. | | 2009/0216100 A1 | 8/2009 | Ebner et al. |
| 2008/0287766 A1 | 11/2008 | Rasdal et al. | | 2009/0216103 A1 | 8/2009 | Brister et al. |
| 2008/0288180 A1 | 11/2008 | Hayter | | 2009/0234200 A1 | 9/2009 | Husheer |
| 2008/0288204 A1 | 11/2008 | Hayter et al. | | 2009/0240120 A1 | 9/2009 | Mensinger et al. |
| 2008/0296155 A1 | 12/2008 | Shults et al. | | 2009/0240128 A1 | 9/2009 | Mensinger et al. |
| 2008/0306368 A1 | 12/2008 | Goode et al. | | 2009/0240193 A1 | 9/2009 | Mensinger et al. |
| 2008/0306434 A1 | 12/2008 | Dobbles et al. | | 2009/0242399 A1 | 10/2009 | Kamath et al. |
| 2008/0306435 A1 | 12/2008 | Kamath et al. | | 2009/0242425 A1 | 10/2009 | Kamath et al. |
| 2008/0306444 A1 | 12/2008 | Brister et al. | | 2009/0247855 A1 | 10/2009 | Boock et al. |
| 2008/0312518 A1 | 12/2008 | Jina et al. | | 2009/0247856 A1 | 10/2009 | Boock et al. |
| 2008/0312841 A1 | 12/2008 | Hayter | | 2009/0247931 A1 | 10/2009 | Damgaard-Sorensen |
| 2008/0312842 A1 | 12/2008 | Hayter | | 2009/0267765 A1 | 10/2009 | Greene et al. |
| 2008/0312844 A1 | 12/2008 | Hayter et al. | | 2009/0287073 A1 | 11/2009 | Boock et al. |
| 2008/0312845 A1 | 12/2008 | Hayter et al. | | 2009/0287074 A1 | 11/2009 | Shults et al. |
| 2009/0005665 A1 | 1/2009 | Hayter et al. | | 2009/0289796 A1 | 11/2009 | Blumberg |
| 2009/0005666 A1 | 1/2009 | Shin et al. | | 2009/0298182 A1 | 12/2009 | Schulat et al. |
| 2009/0006034 A1 | 1/2009 | Hayter et al. | | 2009/0299155 A1 | 12/2009 | Yang et al. |
| 2009/0012379 A1 | 1/2009 | Goode et al. | | 2009/0299156 A1 | 12/2009 | Simpson et al. |
| 2009/0018424 A1 | 1/2009 | Kamath et al. | | 2009/0299162 A1 | 12/2009 | Brauker et al. |
| 2009/0018425 A1 | 1/2009 | Ouyang et al. | | 2009/0299276 A1 | 12/2009 | Brauker et al. |
| 2009/0030294 A1 | 1/2009 | Petisce et al. | | 2010/0010324 A1 | 1/2010 | Brauker et al. |
| 2009/0033482 A1 | 2/2009 | Hayter et al. | | 2010/0010331 A1 | 1/2010 | Brauker et al. |
| 2009/0036747 A1 | 2/2009 | Hayter et al. | | 2010/0010332 A1 | 1/2010 | Brauker et al. |
| 2009/0036758 A1 | 2/2009 | Brauker et al. | | 2010/0016687 A1 | 1/2010 | Brauker et al. |
| 2009/0036760 A1 | 2/2009 | Hayter | | 2010/0016698 A1 | 1/2010 | Rasdal et al. |
| 2009/0036763 A1 | 2/2009 | Brauker et al. | | 2010/0022855 A1 | 1/2010 | Brauker et al. |
| 2009/0043181 A1 | 2/2009 | Brauker et al. | | 2010/0030038 A1 | 2/2010 | Brauker et al. |
| 2009/0043182 A1 | 2/2009 | Brauker et al. | | 2010/0030053 A1 | 2/2010 | Goode, Jr. et al. |
| 2009/0043525 A1 | 2/2009 | Brauker et al. | | 2010/0030484 A1 | 2/2010 | Brauker et al. |
| 2009/0043541 A1 | 2/2009 | Brauker et al. | | 2010/0030485 A1 | 2/2010 | Brauker et al. |
| 2009/0043542 A1 | 2/2009 | Brauker et al. | | 2010/0036215 A1 | 2/2010 | Goode, Jr. et al. |
| 2009/0045055 A1 | 2/2009 | Rhodes et al. | | 2010/0036216 A1 | 2/2010 | Goode, Jr. et al. |
| 2009/0048503 A1 | 2/2009 | Dalal et al. | | 2010/0036222 A1 | 2/2010 | Goode, Jr. et al. |
| 2009/0055149 A1 | 2/2009 | Hayter et al. | | 2010/0036223 A1 | 2/2010 | Goode, Jr. et al. |
| 2009/0062633 A1 | 3/2009 | Brauker et al. | | 2010/0036225 A1 | 2/2010 | Goode, Jr. et al. |
| 2009/0062635 A1 | 3/2009 | Brauker et al. | | 2010/0041971 A1 | 2/2010 | Goode, Jr. et al. |
| 2009/0062767 A1 | 3/2009 | VanAntwerp et al. | | 2010/0045465 A1 | 2/2010 | Brauker et al. |
| 2009/0063402 A1 | 3/2009 | Hayter | | 2010/0049024 A1 | 2/2010 | Saint et al. |
| 2009/0076356 A1 | 3/2009 | Simpson et al. | | 2010/0057040 A1 | 3/2010 | Hayter |
| 2009/0076360 A1 | 3/2009 | Brister et al. | | 2010/0057041 A1 | 3/2010 | Hayter |
| 2009/0076361 A1 | 3/2009 | Kamath et al. | | 2010/0057042 A1 | 3/2010 | Hayter |
| 2009/0085768 A1 | 4/2009 | Patel et al. | | 2010/0057044 A1 | 3/2010 | Hayter |
| 2009/0085873 A1* | 4/2009 | Betts et al. .................... 345/169 | | 2010/0057057 A1 | 3/2010 | Hayter et al. |
| 2009/0099436 A1 | 4/2009 | Brister et al. | | 2010/0063373 A1 | 3/2010 | Kamath et al. |

| | | | |
|---|---|---|---|
| 2010/0076283 A1 | 3/2010 | Simpson et al. |
| 2010/0081906 A1 | 4/2010 | Hayter et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0119693 A1 | 5/2010 | Tapsak et al. |
| 2010/0121169 A1 | 5/2010 | Petisce et al. |
| 2010/0160759 A1 | 6/2010 | Celentano et al. |
| 2010/0168538 A1 | 7/2010 | Keenan et al. |
| 2010/0190435 A1 | 7/2010 | Cook et al. |
| 2011/0004276 A1 | 1/2011 | Blair et al. |
| 2011/0148905 A1 | 6/2011 | Simmons et al. |
| 2011/0152637 A1 | 6/2011 | Kateraas et al. |
| 2011/0257895 A1 | 10/2011 | Brauker et al. |

FOREIGN PATENT DOCUMENTS

| | | |
|---|---|---|
| CA | 2413148 | 8/2010 |
| DE | 4401400 | 7/1995 |
| EP | 0098592 | 1/1984 |
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 0724859 | 8/1996 |
| EP | 0678308 | 5/2000 |
| EP | 1048264 | 11/2000 |
| EP | 1292218 | 3/2003 |
| EP | 1077634 | 7/2003 |
| EP | 1666091 | 6/2006 |
| EP | 1703697 | 9/2006 |
| EP | 1704893 | 9/2006 |
| EP | 1897487 | 11/2009 |
| EP | 1897492 | 11/2009 |
| EP | 2113864 | 11/2009 |
| EP | 1897488 | 12/2009 |
| EP | 1681992 | 4/2010 |
| EP | 1448489 | 8/2010 |
| EP | 1971396 | 8/2010 |
| EP | 2201969 | 3/2011 |
| EP | 2153382 | 2/2012 |
| EP | 2284773 | 2/2012 |
| WO | WO-93/06237 | 4/1993 |
| WO | WO-96/25089 | 8/1996 |
| WO | WO-96/35370 | 11/1996 |
| WO | WO-97/33513 | 9/1997 |
| WO | WO-98/35053 | 8/1998 |
| WO | WO-99/56613 | 11/1999 |
| WO | WO-00/49940 | 8/2000 |
| WO | WO-00/59370 | 10/2000 |
| WO | WO-00/74753 | 12/2000 |
| WO | WO-00/78992 | 12/2000 |
| WO | WO-01/52935 | 7/2001 |
| WO | WO-01/54753 | 8/2001 |
| WO | WO-02/16905 | 2/2002 |
| WO | WO-02/058537 | 8/2002 |
| WO | WO-03/076893 | 9/2003 |
| WO | WO-03/082091 | 10/2003 |
| WO | WO-03/085372 | 10/2003 |
| WO | WO-2004/047445 | 6/2004 |
| WO | WO-2004/061420 | 7/2004 |
| WO | WO-2005/040404 | 5/2005 |
| WO | WO-2005/041766 | 5/2005 |
| WO | WO-2005/045744 | 5/2005 |
| WO | WO-2005/089103 | 9/2005 |
| WO | WO-2006/024671 | 3/2006 |
| WO | WO-2006/032653 | 3/2006 |
| WO | WO-2006/064397 | 6/2006 |
| WO | WO-2006/124099 | 11/2006 |
| WO | WO-2008/086541 | 7/2008 |
| WO | WO-2008/138006 | 11/2008 |
| WO | WO-2011/022418 | 2/2011 |

OTHER PUBLICATIONS

Isermann, R., et al., "Trends in the Application of Model-Based Fault Detection and Diagnosis of Technical Processes", Control Engineering Practice, vol. 5, No. 5, 1997, pp. 709-719.

Kaplan, S. M., "Wiley Electrical and Electronics Engineering Dictionary", IEEE Press, 2004, pp. 141, 142, 548, 549.

Lortz, J., et al., "What is Bluetooth? We Explain the Newest Short-Range Connectivity Technology", Smart Computing Learning Series, Wireless Computing, vol. 8, Issue 5, 2002, pp. 72-74.

PCT Application No. PCT/US2009/045545, International Search Report and Written Opinion of the International Searching Authority mailed Jul. 20, 2009.

PCT Application No. PCT/US2009/045545, International Preliminary Report on Patentability and Written Opinion of the International Searching Authority mailed Dec. 9, 2010.

U.S. Appl. No. 12/130,995, Office Action mailed Apr. 6, 2010.

U.S. Appl. No. 12/130,995, Notice of Allowance mailed Aug. 27, 2010.

U.S. Appl. No. 12/130,995, Supplemental Notice of Allowance mailed Sep. 16, 2010.

Lo, B., et al., "Key Technical Challenges and Current Implementations of Body Sensor Networks", *Body Sensor Networks*, 2005, pp. 1-5.

Lodwig, V., et al., "Continuous Glucose Monitoring with Glucose Sensors: Calibration and Assessment Criteria", *Diabetes Technology & Therapeutics*, vol. 5, No. 4, 2003, pp. 573-587.

Rodriguez, N., et al., "Flexible Communication and Control Protocol for Injectable Neuromuscular Interfaces", *IEEE Transactions on Biomedical Circuits and Systems*, vol. 1, No. 1, 2007, pp. 19-27.

Tung, S., "Layers of Security for Active RFID Tags", *RFID Handbook: Applications, Technology, Security, and Privacy*, Chapter 33, 2008, pp. 1-28.

Chinese Patent Application No. 20090129741.7, Office Action mailed May 28, 2012.

European Patent Application No. EP09755752.4, Extended European Search Report mailed Mar. 14, 2012.

\* cited by examiner

CLOSE PROXIMITY COMMUNICATION DEVICE AND METHODS

RELATED APPLICATION

The present application is a continuation of U.S. patent application Ser. No. 12/130,995 filed May 30, 2008, now U.S. Pat. No. 7,826,382, entitled "Close Proximity Communication Device and Methods", the disclosure of which is incorporated herein by reference for all purposes.

BACKGROUND

Analyte, e.g., glucose monitoring systems including continuous and discrete monitoring systems generally include a small, lightweight battery powered and microprocessor controlled system which is configured to detect signals proportional to the corresponding measured glucose levels using an electrometer. RF signals may be used to transmit the collected data. One aspect of certain analyte monitoring systems include a transcutaneous or subcutaneous analyte sensor configuration which is, for example, at least partially positioned through the skin layer of a subject whose analyte level is to be monitored. The sensor may use a two or three-electrode (work, reference and counter electrodes) configuration driven by a controlled potential (potentiostat) analog circuit connected through a contact system.

An analyte sensor may be configured so that a portion thereof is placed under the skin of the patient so as to contact analyte of the patient, and another portion or segment of the analyte sensor may be in communication with the transmitter unit. The transmitter unit may be configured to transmit the analyte levels detected by the sensor over a wireless communication link such as an RF (radio frequency) communication link to a receiver/monitor unit. The receiver/monitor unit may perform data analysis, among other functions, on the received analyte levels to generate information pertaining to the monitored analyte levels.

Transmission of control or command data over wireless communication link is often constrained to occur within a substantially short time duration. In turn, the time constraint in data communication imposes limits on the type and size of data that may be transmitted during the transmission time period.

In view of the foregoing, it would be desirable to have a method and apparatus for optimizing the RF communication link between two or more communication devices, for example, in a medical communication system.

SUMMARY

Devices and methods for analyte monitoring, e.g., glucose monitoring, and/or therapy management system including, for example, medication infusion device are provided. Embodiments include transmitting information from a first location to a second, e.g., using a telemetry system such as RF telemetry. Systems herein include continuous analyte monitoring systems, discrete analyte monitoring systems, and therapy management systems.

These and other objects, features and advantages of the present disclosure will become more fully apparent from the following detailed description of the embodiments, the appended claims and the accompanying drawings.

DETAILED DESCRIPTION

As summarized above and as described in further detail below, in accordance with the various embodiments of the present disclosure, there is provided a method and system for positioning a controller unit within a transmission range for close proximity communication, transmitting one or more predefined close proximity commands, and receiving a response packet in response to the transmitted one or more predefined close proximity commands.

Figure 1:
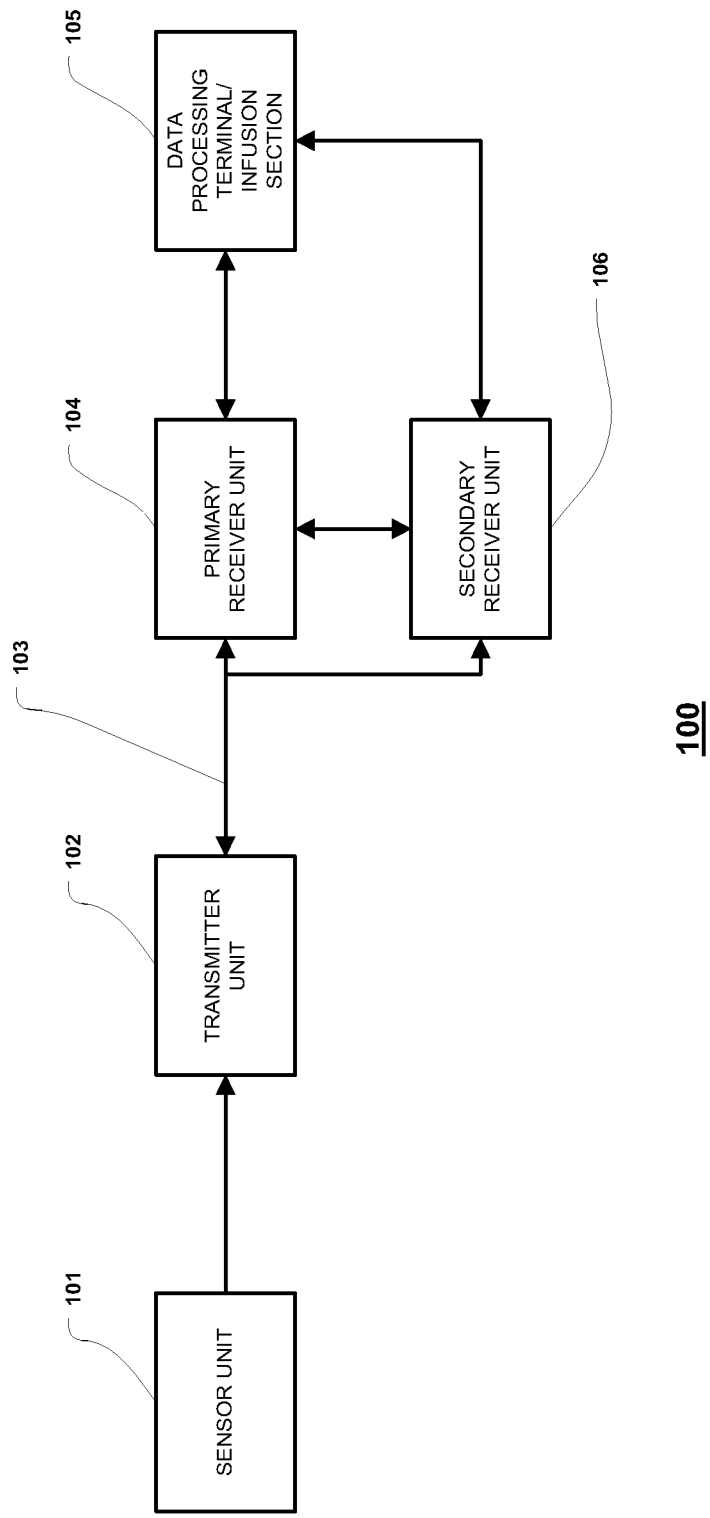
FIG. 1 illustrates a block diagram of a data monitoring and management system for practicing one or more embodiments of the present disclosure.

FIG. 1 illustrates a data monitoring and management system such as, for example, analyte (e.g., glucose) monitoring system 100 in accordance with one embodiment of the present disclosure. The subject invention is further described primarily with respect to a glucose monitoring system for convenience and such description is in no way intended to limit the scope of the invention. It is to be understood that the analyte monitoring system may be configured to monitor a variety of analytes, e.g., lactate, and the like.

Analytes that may be monitored include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. More than one analyte may be monitored by a single system, e.g. a single analyte sensor.

The analyte monitoring system 100 includes a sensor unit 101, a transmitter unit 102 coupleable to the sensor unit 101, and a primary receiver unit 104 which is configured to communicate with the transmitter unit 102 via a bi-directional communication link 103. The primary receiver unit 104 may be further configured to transmit data to a data processing terminal 105 for evaluating the data received by the primary receiver unit 104. Moreover, the data processing terminal 105 in one embodiment may be configured to receive data directly from the transmitter unit 102 via a communication link which may optionally be configured for bi-directional communication. Accordingly, transmitter unit 102 and/or receiver unit 104 may include a transceiver.

Also shown in FIG. 1 is an optional secondary receiver unit 106 which is operatively coupled to the communication link and configured to receive data transmitted from the transmitter unit 102. Moreover, as shown in the Figure, the secondary receiver unit 106 is configured to communicate with the primary receiver unit 104 as well as the data processing terminal 105. Indeed, the secondary receiver unit 106 may be configured for bi-directional wireless communication with each or one of the primary receiver unit 104 and the data processing terminal 105. As discussed in further detail below, in one embodiment of the present disclosure, the secondary receiver unit 106 may be configured to include a limited number of functions and features as compared with the primary receiver unit 104. As such, the secondary receiver unit 106 may be configured substantially in a smaller compact housing or embodied in a device such as a wrist watch, pager, mobile phone, PDA, for example. Alternatively, the secondary receiver unit 106 may be configured with the same or substantially similar functionality as the primary receiver unit 104. The receiver unit may be configured to be used in conjunction with a docking cradle unit, for example for one or more of the following or other functions: placement by bedside, for re-charging, for data management, for night time monitoring, and/or bi-directional communication device.

In one aspect sensor unit 101 may include two or more sensors, each configured to communicate with transmitter unit 102. Furthermore, while only one, transmitter unit 102, communication link 103, and data processing terminal 105 are shown in the embodiment of the analyte monitoring system 100 illustrated in FIG. 1, it will be appreciated by one of ordinary skill in the art that the analyte monitoring system 100 may include one or more sensors 101, multiple transmitter units 102, communication links 103, and data processing terminals 105. Moreover, within the scope of the present disclosure, the analyte monitoring system 100 may be a continuous monitoring system, or semi-continuous, or a discrete monitoring system. In a multi-component environment, each device is configured to be uniquely identified by each of the other devices in the system so that communication conflict is readily resolved between the various components within the analyte monitoring system 100.

In one embodiment of the present disclosure, the sensor unit 101 is physically positioned in or on the body of a user whose analyte level is being monitored. The sensor unit 101 may be configured to continuously sample the analyte level of the user and convert the sampled analyte level into a corresponding data signal for transmission by the transmitter unit 102. In certain embodiments, the transmitter unit 102 may be physically coupled to the sensor unit 101 so that both devices are integrated in a single housing and positioned on the user's body. The transmitter unit 102 may perform data processing such as filtering and encoding on data signals and/or other functions, each of which corresponds to a sampled analyte level of the user, and in any event transmitter unit 102 transmits analyte information to the primary receiver unit 104 via the communication link 103.

In one embodiment, the analyte monitoring system 100 is configured as a one-way RF communication path from the transmitter unit 102 to the primary receiver unit 104. In such embodiment, the transmitter unit 102 transmits the sampled data signals received from the sensor unit 101 without acknowledgement from the primary receiver unit 104 that the transmitted sampled data signals have been received. For example, the transmitter unit 102 may be configured to transmit the encoded sampled data signals at a fixed rate (e.g., at one minute intervals) after the completion of the initial power on procedure. Likewise, the primary receiver unit 104 may be configured to detect such transmitted encoded sampled data signals at predetermined time intervals. Alternatively, the analyte monitoring system 100 may be configured with a bi-directional RF (or otherwise) communication between the transmitter unit 102 and the primary receiver unit 104.

Additionally, in one aspect, the primary receiver unit 104 may include two sections. The first section is an analog interface section that is configured to communicate with the transmitter unit 102 via the communication link 103. In one embodiment, the analog interface section may include an RF receiver and an antenna for receiving and amplifying the data signals from the transmitter unit 102, which are thereafter, demodulated with a local oscillator and filtered through a band-pass filter. The second section of the primary receiver unit 104 is a data processing section which is configured to process the data signals received from the transmitter unit 102 such as by performing data decoding, error detection and correction, data clock generation, and data bit recovery.

In operation, upon completing the power-on procedure, the primary receiver unit 104 is configured to detect the presence of the transmitter unit 102 within its range based on, for example, the strength of the detected data signals received from the transmitter unit 102 and/or a predetermined transmitter identification information. Upon successful synchronization with the corresponding transmitter unit 102, the primary receiver unit 104 is configured to begin receiving from the transmitter unit 102 data signals corresponding to the user's detected analyte level. More specifically, the primary receiver unit 104 in one embodiment is configured to perform synchronized time hopping with the corresponding synchronized transmitter unit 102 via the communication link 103 to obtain the user's detected analyte level.

Referring again to FIG. 1, the data processing terminal 105 may include a personal computer, a portable computer such as a laptop or a handheld device (e.g., personal digital assistants (PDAs)), and the like, each of which may be configured for data communication with the receiver via a wired or a wireless connection. Additionally, the data processing terminal 105 may further be connected to a data network (not shown) for storing, retrieving and updating data corresponding to the detected analyte level of the user.

Within the scope of the present disclosure, the data processing terminal 105 may include an infusion device such as an insulin infusion pump (external or implantable) or the like, which may be configured to administer insulin to patients, and which may be configured to communicate with the receiver unit 104 for receiving, among others, the measured analyte level. Alternatively, the receiver unit 104 may be configured to integrate or otherwise couple to an infusion device therein so that the receiver unit 104 is configured to administer insulin therapy to patients, for example, for administering and modifying basal profiles, as well as for determining appropriate boluses for administration based on, among others, the detected analyte levels received from the transmitter unit 102.

Additionally, the transmitter unit 102, the primary receiver unit 104 and the data processing terminal 105 may each be configured for bi-directional wireless communication such that each of the transmitter unit 102, the primary receiver unit 104 and the data processing terminal 105 may be configured to communicate (that is, transmit data to and receive data from) with each other via a wireless communication link. More specifically, the data processing terminal 105 may in one embodiment be configured to receive data directly from the transmitter unit 102 via a communication link, where the communication link, as described above, may be configured for bi-directional communication.

In this embodiment, the data processing terminal 105, which may include an insulin pump, may be configured to receive the analyte signals from the transmitter unit 102, and thus, incorporate the functions of the receiver 104 including data processing for managing the patient's insulin therapy and analyte monitoring. In one embodiment, the communication link 103 may include one or more of an RF communication protocol, an infrared communication protocol, a Bluetooth® enabled communication protocol, an 802.11x wireless communication protocol, or an equivalent wireless communication protocol which would allow secure, wireless communication of several units (for example, per HIPAA requirements) while avoiding potential data collision and interference.

Figure 2:
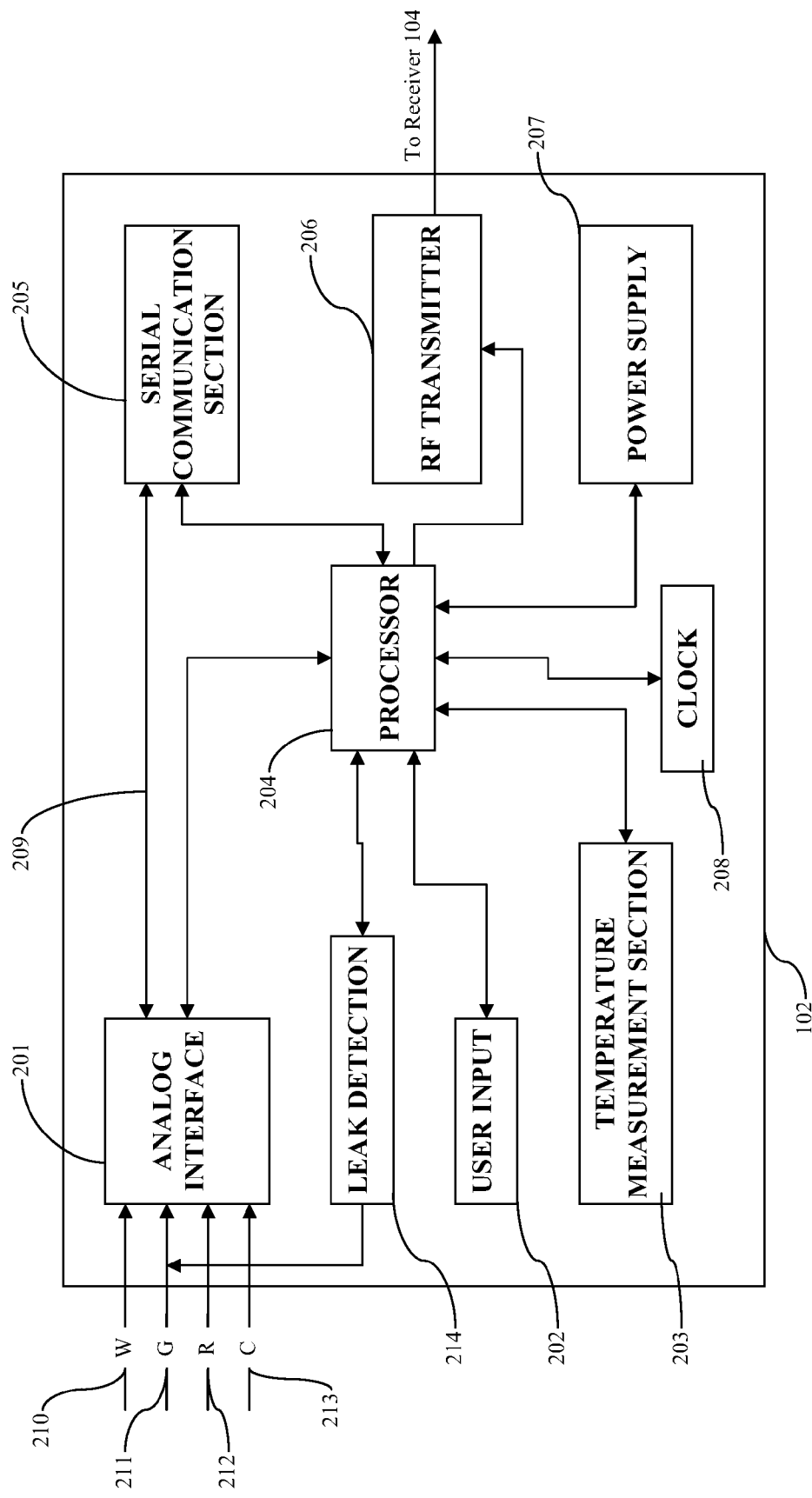
FIG. 2 is a block diagram of the transmitter unit of the data monitoring and management system shown in FIG. 1 in accordance with one embodiment of the present disclosure.

FIG. 2 is a block diagram of the transmitter of the data monitoring and detection system shown in FIG. 1 in accordance with one embodiment of the present disclosure. Referring to the Figure, the transmitter unit 102 in one embodiment includes an analog interface 201 configured to communicate with the sensor unit 101 (FIG. 1), a user input 202, and a temperature detection section 203, each of which is operatively coupled to a transmitter processor 204 such as a central processing unit (CPU). As can be seen from FIG. 2, there are provided four contacts, three of which are electrodes—work electrode (W) 210, guard contact (G) 211, reference electrode (R) 212, and counter electrode (C) 213, each operatively coupled to the analog interface 201 of the transmitter unit 102 for connection to the sensor unit 101 (FIG. 1). In one embodiment, each of the work electrode (W) 210, guard contact (G) 211, reference electrode (R) 212, and counter electrode (C) 213 may be made using a conductive material that is either printed or etched or ablated, for example, such as carbon which may be printed, or a metal such as a metal foil (e.g., gold) or the like, which may be etched or ablated or otherwise processed to provide one or more electrodes. Fewer or greater electrodes and/or contact may be provided in certain embodiments.

Further shown in FIG. 2 are a transmitter serial communication section 205 and an RF transmitter 206, each of which is also operatively coupled to the transmitter processor 204. Moreover, a power supply 207 such as a battery is also provided in the transmitter unit 102 to provide the necessary power for the transmitter unit 102. Additionally, as can be seen from the Figure, clock 208 is provided to, among others, supply real time information to the transmitter processor 204.

In one embodiment, a unidirectional input path is established from the sensor unit 101 (FIG. 1) and/or manufacturing and testing equipment to the analog interface 201 of the transmitter unit 102, while a unidirectional output is established from the output of the RF transmitter 206 of the transmitter unit 102 for transmission to the primary receiver unit 104. In this manner, a data path is shown in FIG. 2 between the aforementioned unidirectional input and output via a dedicated link 209 from the analog interface 201 to serial communication section 205, thereafter to the processor 204, and then to the RF transmitter 206. As such, in one embodiment, via the data path described above, the transmitter unit 102 is configured to transmit to the primary receiver unit 104 (FIG. 1), via the communication link 103 (FIG. 1), processed and encoded data signals received from the sensor unit 101 (FIG. 1). Additionally, the unidirectional communication data path between the analog interface 201 and the RF transmitter 206 discussed above allows for the configuration of the transmitter unit 102 for operation upon completion of the manufacturing process as well as for direct communication for diagnostic and testing purposes.

As discussed above, the transmitter processor 204 is configured to transmit control signals to the various sections of the transmitter unit 102 during the operation of the transmitter unit 102. In one embodiment, the transmitter processor 204 also includes a memory (not shown) for storing data such as the identification information for the transmitter unit 102, as well as the data signals received from the sensor unit 101. The stored information may be retrieved and processed for transmission to the primary receiver unit 104 under the control of the transmitter processor 204. Furthermore, the power supply 207 may include a commercially available battery, which may be a rechargeable battery.

In certain embodiments, the transmitter unit 102 is also configured such that the power supply section 207 is capable of providing power to the transmitter for a minimum of about three months of continuous operation, e.g., after having been stored for about eighteen months such as stored in a low-power (non-operating) mode. In one embodiment, this may be achieved by the transmitter processor 204 operating in low power modes in the non-operating state, for example, drawing no more than approximately 1 µA of current. Indeed, in one embodiment, a step during the manufacturing process of the transmitter unit 102 may place the transmitter unit 102 in the lower power, non-operating state (i.e., post-manufacture sleep mode). In this manner, the shelf life of the transmitter unit 102 may be significantly improved. Moreover, as shown in FIG. 2, while the power supply unit 207 is shown as coupled to the processor 204, and as such, the processor 204 is configured to provide control of the power supply unit 207, it should be noted that within the scope of the present disclosure, the power supply unit 207 is configured to provide the necessary power to each of the components of the transmitter unit 102 shown in FIG. 2.

Referring back to FIG. 2, the power supply section 207 of the transmitter unit 102 in one embodiment may include a rechargeable battery unit that may be recharged by a separate power supply recharging unit (for example, provided in the receiver unit 104) so that the transmitter unit 102 may be powered for a longer period of usage time. Moreover, in one embodiment, the transmitter unit 102 may be configured without a battery in the power supply section 207, in which case the transmitter unit 102 may be configured to receive power from an external power supply source (for example, a battery) as discussed in further detail below.

Referring yet again to FIG. 2, the temperature detection section 203 of the transmitter unit 102 is configured to monitor the temperature of the skin near the sensor insertion site. The temperature reading is used to adjust the analyte readings obtained from the analog interface 201. In certain embodiments, the RF transmitter 206 of the transmitter unit 102 may be configured for operation in the frequency band of approximately 315 MHz to approximately 322 MHz, for example, in the United States. In certain embodiments, the RF transmitter 206 of the transmitter unit 102 may be configured for operation in the frequency band of approximately 400 MHz to approximately 470 MHz. Further, in one embodiment, the RF transmitter 206 is configured to modulate the carrier frequency by performing Frequency Shift Keying and Manchester encoding. In one embodiment, the data transmission rate is about 19,200 symbols per second, with a minimum transmission range for communication with the primary receiver unit 104.

Referring yet again to FIG. 2, also shown is a leak detection circuit 214 coupled to the guard contact (G) 211 and the processor 204 in the transmitter unit 102 of the data monitoring and management system 100. The leak detection circuit 214 in accordance with one embodiment of the present disclosure may be configured to detect leakage current in the sensor unit 101 to determine whether the measured sensor data is corrupt or whether the measured data from the sensor 101 is accurate. Exemplary analyte systems that may be employed are described in, for example, U.S. Pat. Nos. 6,134,461, 6,175,752, 6,121,611, 6,560,471, 6,746,582, and elsewhere, the disclosure of each of which are incorporated by reference for all purposes.

Figure 3:
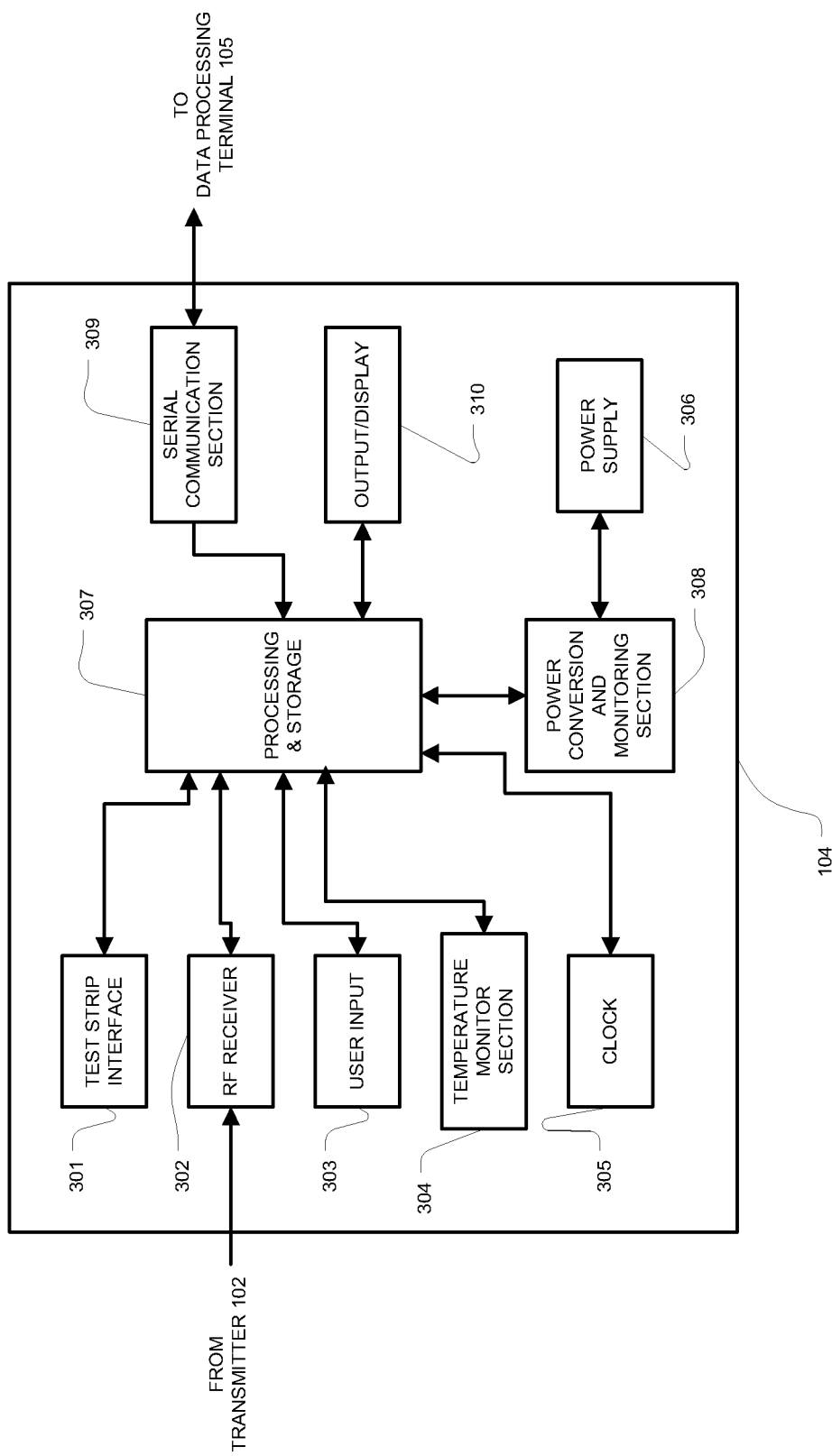
FIG. 3 is a block diagram of the receiver/monitor unit of the data monitoring and management system shown in FIG. 1 in accordance with one embodiment of the present disclosure.

FIG. 3 is a block diagram of the receiver/monitor unit of the data monitoring and management system shown in FIG. 1 in accordance with one embodiment of the present disclosure. Referring to FIG. 3, the primary receiver unit 104 includes an analyte test strip, e.g., blood glucose test strip, interface 301, an RF receiver 302, an input 303, a temperature detection section 304, and a clock 305, each of which is operatively coupled to a receiver processor 307. As can be further seen from the Figure, the primary receiver unit 104 also includes a power supply 306 operatively coupled to a power conversion and monitoring section 308. Further, the power conversion and monitoring section 308 is also coupled to the receiver processor 307. Moreover, also shown are a receiver serial communication section 309, and an output 310, each operatively coupled to the receiver processor 307.

In one embodiment, the test strip interface 301 includes a glucose level testing portion to receive a manual insertion of a glucose test strip, and thereby determine and display the glucose level of the test strip on the output 310 of the primary receiver unit 104. This manual testing of glucose may be used to calibrate the sensor unit 101 or otherwise. The RF receiver 302 is configured to communicate, via the communication link 103 (FIG. 1) with the RF transmitter 206 of the transmitter unit 102, to receive encoded data signals from the transmitter unit 102 for, among others, signal mixing, demodulation, and other data processing. The input 303 of the primary receiver unit 104 is configured to allow the user to enter information into the primary receiver unit 104 as needed. In one aspect, the input 303 may include one or more keys of a keypad, a touch-sensitive screen, or a voice-activated input command unit. The temperature detection section 304 is configured to provide temperature information of the primary receiver unit 104 to the receiver processor 307, while the clock 305 provides, among others, real time information to the receiver processor 307.

Each of the various components of the primary receiver unit 104 shown in FIG. 3 is powered by the power supply 306 which, in one embodiment, includes a battery. Furthermore, the power conversion and monitoring section 308 is configured to monitor the power usage by the various components in the primary receiver unit 104 for effective power management and to alert the user, for example, in the event of power usage which renders the primary receiver unit 104 in sub-optimal operating conditions. An example of such sub-optimal operating condition may include, for example, operating the vibration output mode (as discussed below) for a period of time thus substantially draining the power supply 306 while the processor 307 (thus, the primary receiver unit 104) is turned on. Moreover, the power conversion and monitoring section 308 may additionally be configured to include a reverse polarity protection circuit such as a field effect transistor (FET) configured as a battery activated switch.

The serial communication section 309 in the primary receiver unit 104 is configured to provide a bi-directional communication path from the testing and/or manufacturing equipment for, among others, initialization, testing, and configuration of the primary receiver unit 104. Serial communication section 309 can also be used to upload data to a computer, such as time-stamped blood glucose data. The communication link with an external device (not shown) can be made, for example, by cable, infrared (IR) or RF link. The output 310 of the primary receiver unit 104 is configured to provide, among others, a graphical user interface (GUI) such as a liquid crystal display (LCD) for displaying information. Additionally, the output 310 may also include an integrated speaker for outputting audible signals as well as to provide vibration output as commonly found in handheld electronic devices, such as mobile telephones presently available. In a further embodiment, the primary receiver unit 104 also includes an electro-luminescent lamp configured to provide backlighting to the output 310 for output visual display in dark ambient surroundings.

Referring back to FIG. 3, the primary receiver unit 104 in one embodiment may also include a storage section such as a programmable, non-volatile memory device as part of the processor 307, or provided separately in the primary receiver unit 104, operatively coupled to the processor 307. The processor 307 may be configured to synchronize with a transmitter, e.g., using Manchester decoding or the like, as well as error detection and correction upon the encoded data signals received from the transmitter unit 102 via the communication link 103.

Additional description of the RF communication between the transmitter 102 and the primary receiver 104 (or with the secondary receiver 106) that may be employed in embodiments of the subject invention is disclosed in pending application Ser. No. 11/060,365 filed Feb. 16, 2005 entitled "Method and System for Providing Data Communication in Continuous Glucose Monitoring and Management System" the disclosure of which is incorporated herein by reference for all purposes.

Referring to the Figures, in one embodiment, the transmitter 102 (FIG. 1) may be configured to generate data packets for periodic transmission to one or more of the receiver units 104, 106, where each data packet includes in one embodiment two categories of data—urgent data and non-urgent data. For example, urgent data such as for example glucose data from the sensor and/or temperature data associated with the sensor may be packed in each data packet in addition to non-urgent data, where the non-urgent data is rolled or varied with each data packet transmission.

That is, the non-urgent data is transmitted at a timed interval so as to maintain the integrity of the analyte monitoring system without being transmitted over the RF communication link with each data transmission packet from the transmitter 102. In this manner, the non-urgent data, for example that is not time sensitive, may be periodically transmitted (and not with each data packet transmission) or broken up into predetermined number of segments and sent or transmitted over multiple packets, while the urgent data is transmitted substantially in its entirety with each data transmission.

Referring again to the Figures, upon receiving the data packets from the transmitter 102, the one or more receiver units 104, 106 may be configured to parse the received data packet to separate the urgent data from the non-urgent data, and also, may be configured to store the urgent data and the non-urgent data, e.g., in a hierarchical manner. In accordance with the particular configuration of the data packet or the data transmission protocol, more or less data may be transmitted as part of the urgent data, or the non-urgent rolling data. That is, within the scope of the present disclosure, the specific data packet implementation such as the number of bits per packet, and the like, may vary based on, among others, the communication protocol, data transmission time window, and so on.

In an exemplary embodiment, different types of data packets may be identified accordingly. For example, identification in certain exemplary embodiments may include—(1) single sensor, one minute of data, (2) two or multiple sensors, (3) dual sensor, alternate one minute data, and (4) response packet. For single sensor one minute data packet, in one embodiment, the transmitter 102 may be configured to generate the data packet in the manner, or similar to the manner, shown in Table 1 below.

TABLE 1

Single sensor, one minute of data

| Number of Bits | Data Field |
|---|---|
| 8 | Transmit Time |
| 14 | Sensor1 Current Data |
| 14 | Sensor1 Historic Data |
| 8 | Transmit Status |
| 12 | AUX Counter |
| 12 | AUX Thermistor 1 |
| 12 | AUX Thermistor 2 |
| 8 | Rolling-Data-1 |

As shown in Table 1 above, the transmitter data packet in one embodiment may include 8 bits of transmit time data, 14 bits of current sensor data, 14 bits of preceding sensor data, 8 bits of transmitter status data, 12 bits of auxiliary counter data, 12 bits of auxiliary thermistor 1 data, 12 bits of auxiliary thermistor 2 data and 8 bits of rolling data. In one embodiment of the present disclosure, the data packet generated by the transmitter for transmission over the RF communication link may include all or some of the data shown above in Table 1.

Referring back, the 14 bits of the current sensor data provides the real time or current sensor data associated with the detected analyte level, while the 14 bits of the sensor historic or preceding sensor data includes the sensor data associated with the detected analyte level one minute ago. In this manner, in the case where the receiver unit 104, 106 drops or fails to successfully receive the data packet from the transmitter 102 in the minute by minute transmission, the receiver unit 104, 106 may be able to capture the sensor data of a prior minute transmission from a subsequent minute transmission.

Referring again to Table 1, the Auxiliary data in one embodiment may include one or more of the patient's skin temperature data, a temperature gradient data, reference data, and counter electrode voltage. The transmitter status field may include status data that is configured to indicate corrupt data for the current transmission (for example, if shown as BAD status (as opposed to GOOD status which indicates that the data in the current transmission is not corrupt)). Furthermore, the rolling data field is configured to include the non-urgent data, and in one embodiment, may be associated with the time-hop sequence number. In addition, the Transmitter Time field in one embodiment includes a protocol value that is configured to start at zero and is incremented by one with each data packet. In one aspect, the transmitter time data may be used to synchronize the data transmission window with the receiver unit 104, 106, and also, provide an index for the Rolling data field.

In a further embodiment, the transmitter data packet may be configured to provide or transmit analyte sensor data from two or more independent analyte sensors. The sensors may relate to the same or different analyte or property. In such a case, the data packet from the transmitter 102 may be configured to include 14 bits of the current sensor data from both sensors in the embodiment in which 2 sensors are employed. In this case, the data packet does not include the immediately preceding sensor data in the current data packet transmission. Instead, a second analyte sensor data is transmitted with a first analyte sensor data.

TABLE 2

Dual sensor data

| Number of Bits | Data Field |
|---|---|
| 8 | Transmit Time |
| 14 | Sensor1 Current Data |
| 14 | Sensor2 Current Data |
| 8 | Transmit Status |
| 12 | AUX Counter |
| 12 | AUX Thermistor 1 |
| 12 | AUX Thermistor 2 |
| 8 | Rolling-Data-1 |

In a further embodiment, the transmitter data packet may be alternated with each transmission between two analyte sensors, for example, alternating between the data packet shown in Table 3 and Table 4 below.

TABLE 3

Sensor Data Packet Alternate 1

| Number of Bits | Data Field |
|---|---|
| 8 | Transmitter Time |
| 14 | Sensor1 Current Data |
| 14 | Sensor1 Historic Data |
| 8 | Transmit Status |
| 12 | AUX Counter |
| 12 | AUX Thermistor 1 |
| 12 | AUX Thermistor 2 |
| 8 | Rolling-Data-1 |

TABLE 4

Sensor Data Packet Alternate 2

| Number of Bits | Data Field |
|---|---|
| 8 | Transmitter Time |
| 14 | Sensor1 Current Data |
| 14 | Sensor2 Current Data |
| 8 | Transmit Status |
| 12 | AUX Counter |
| 12 | AUX Thermistor 1 |

TABLE 4-continued

Sensor Data Packet Alternate 2

| Number of Bits | Data Field |
|---|---|
| 12 | AUX Thermistor 2 |
| 8 | Rolling-Data-1 |

As shown above in reference to Tables 3 and 4, the minute by minute data packet transmission from the transmitter 102 (FIG. 1) in one embodiment may alternate between the data packet shown in Table 3 and the data packet shown in Table 4. More specifically, the transmitter 102 may be configured in one embodiment to transmit the current sensor data of the first sensor and the preceding sensor data of the first sensor (Table 3), as well as the rolling data, and further, at the subsequent transmission, the transmitter 102 may be configured to transmit the current sensor data of the first and the second sensor in addition to the rolling data.

In one embodiment, the rolling data transmitted with each data packet may include a sequence of various predetermined types of data that are considered not-urgent or not time sensitive. That is, in one embodiment, the following list of data shown in Table 5 may be sequentially included in the 8 bits of transmitter data packet, and not transmitted with each data packet transmission of the transmitter (for example, with each 60 second data transmission from the transmitter 102).

TABLE 5

Rolling Data

| Time Slot | Bits | Rolling-Data |
|---|---|---|
| 0 | 8 | Mode |
| 1 | 8 | Glucose1 Slope |
| 2 | 8 | Glucose2 Slope |
| 3 | 8 | Ref-R |
| 4 | 8 | Hobbs Counter, Ref-R |
| 5 | 8 | Hobbs Counter |
| 6 | 8 | Hobbs Counter |
| 7 | 8 | Sensor Count |

As can be seen from Table 5 above, in one embodiment, a sequence of rolling data are appended or added to the transmitter data packet with each data transmission time slot. In one embodiment, there may be 256 time slots for data transmission by the transmitter 102 (FIG. 1), and where, each time slot is separated by approximately 60 second interval. For example, referring to the Table 5 above, the data packet in transmission time slot 0 (zero) may include operational mode data (Mode) as the rolling data that is appended to the transmitted data packet. At the subsequent data transmission time slot (for example, approximately 60 seconds after the initial time slot (0)), the transmitted data packet may include the analyte sensor 1 calibration factor information (Glucose1 slope) as the rolling data. In this manner, with each data transmission, the rolling data may be updated over the 256 time slot cycle.

Referring again to Table 5, each rolling data field is described in further detail for various embodiments. For example, the Mode data may include information related to the different operating modes such as, but not limited to, the data packet type, the type of battery used, diagnostic routines, single sensor or multiple sensor input, or type of data transmission (RF communication link or other data link such as serial connection). Further, the Glucose1-slope data may include an 8-bit scaling factor or calibration data for first sensor (scaling factor for sensor 1 data), while Glucose2-slope data may include an 8-bit scaling factor or calibration data for the second analyte sensor (in the embodiment including more than one analyte sensors).

In addition, the Ref-R data may include 12 bits of on-board reference resistor used to calibrate our temperature measurement in the thermistor circuit (where 8 bits are transmitted in time slot 3, and the remaining 4 bits are transmitted in time slot 4), and the 20-bit Hobbs counter data may be separately transmitted in three time slots (for example, in time slot 4, time slot 5 and time slot 6) to add up to 20 bits. In one embodiment, the Hobbs counter may be configured to count each occurrence of the data transmission (for example, a packet transmission at approximately 60 second intervals) and may be incremented by a count of one (1).

In one aspect, the Hobbs counter is stored in a nonvolatile memory of the transmitter unit 102 (FIG. 1) and may be used to ascertain the power supply status information such as, for example, the estimated battery life remaining in the transmitter unit 102. That is, with each sensor replacement, the Hobbs counter is not reset, but rather, continues the count with each replacement of the sensor unit 101 to establish contact with the transmitter unit 102 such that, over an extended usage time period of the transmitter unit 102, it may be possible to determine, based on the Hobbs count information, the amount of consumed battery life in the transmitter unit 102, and also, an estimated remaining life of the battery in the transmitter unit 102.

That is, in one embodiment, the 20 bit Hobbs counter is incremented by one each time the transmitter unit 102 transmits a data packet (for example, approximately each 60 seconds), and based on the count information in the Hobbs counter, in one aspect, the battery life of the transmitter unit 102 may be estimated. In this manner, in configurations of the transmitter unit 620 (see FIG. 6) where the power supply is not a replaceable component but rather, embedded within the housing of the transmitter unit 620, it is possible to estimate the remaining life of the embedded battery within the transmitter unit 620. Moreover, the Hobbs counter is configured to remain persistent in the memory device of the transmitter unit 620 such that, even when the transmitter unit power is turned off or powered down (for example, during the periodic sensor unit replacement, RF transmission turned off period and the like), the Hobbs counter information is retained.

Referring to Table 5 above, the transmitted rolling data may also include 8 bits of sensor count information (for example, transmitted in time slot 7). The 8 bit sensor counter is incremented by one each time a new sensor unit is connected to the transmitter unit. The ASIC configuration of the transmitter unit (or a microprocessor based transmitter configuration or with discrete components) may be configured to store in a nonvolatile memory unit the sensor count information and transmit it to the primary receiver unit 104 (for example). In turn, the primary receiver unit 104 (and/or the secondary receiver unit 106) may be configured to determine whether it is receiving data from the transmitter unit that is associated with the same sensor unit (based on the sensor count information), or from a new or replaced sensor unit (which will have a sensor count incremented by one from the prior sensor count). In this manner, in one aspect, the receiver unit (primary or secondary) may be configured to prevent reuse of the same sensor unit by the user based on verifying the sensor count information associated with the data transmission received from the transmitter unit 102. In addition, in a further aspect, user notification may be associated with one or more of these parameters. Further, the receiver unit (primary or secondary) may be configured to detect when a new sensor has been inserted, and thus prevent erroneous application of one or more calibration parameters determined in conjunction with a prior sensor, that may potentially result in false or inaccurate analyte level determination based on the sensor data.

Figure 4:
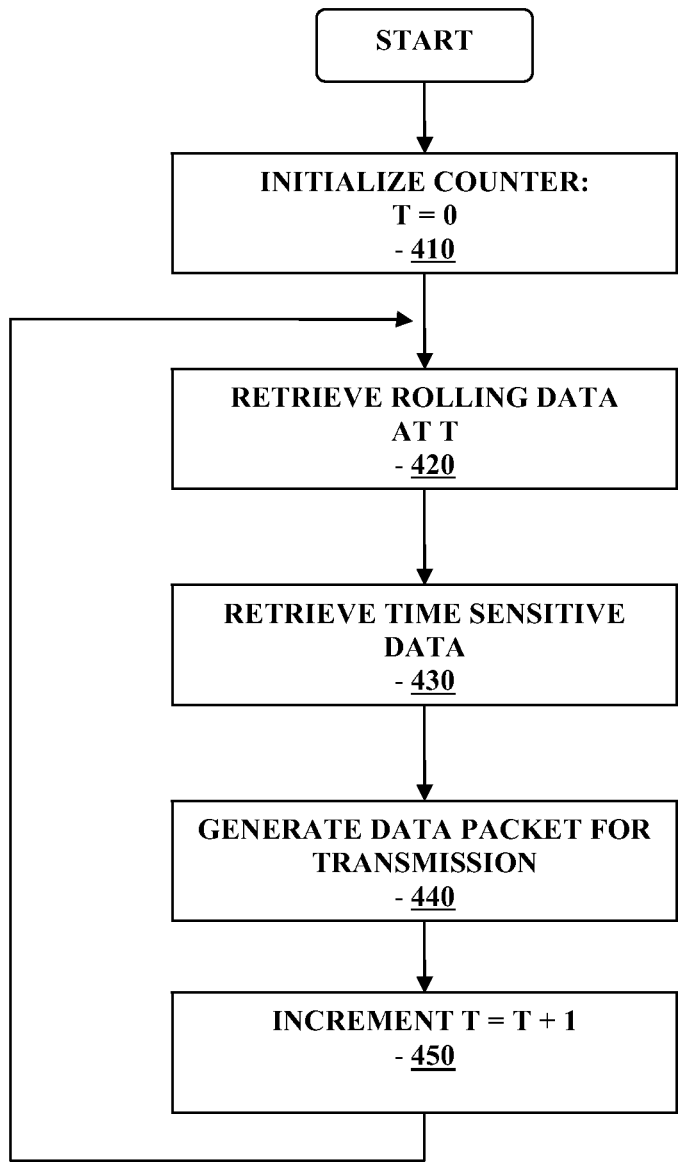
FIG. 4 is a flowchart illustrating data packet procedure including rolling data for transmission in accordance with one embodiment of the present disclosure.

FIG. 4 is a flowchart illustrating a data packet procedure including rolling data for transmission in accordance with one embodiment of the present disclosure. Referring to FIG. 4, in one embodiment, a counter is initialized (for example, to T=0) (410). Thereafter the associated rolling data is retrieved from memory device, for example (420), and also, the time sensitive or urgent data is retrieved (430). In one embodiment, the retrieval of the rolling data (420) and the retrieval of the time sensitive data (430) may be retrieved at substantially the same time.

Referring back to FIG. 4, with the rolling data and the time sensitive data, for example, the data packet for transmission is generated (440), and upon transmission, the counter is incremented by one (450) and the routine returns to retrieval of the rolling data (420). In this manner, in one embodiment, the urgent time sensitive data as well as the non-urgent data may be incorporated in the same data packet and transmitted by the transmitter 102 (FIG. 1) to a remote device such as one or more of the receivers 104, 106. Furthermore, as discussed above, the rolling data may be updated at a predetermined time interval which is longer than the time interval for each data packet transmission from the transmitter 102 (FIG. 1).

Figure 5:
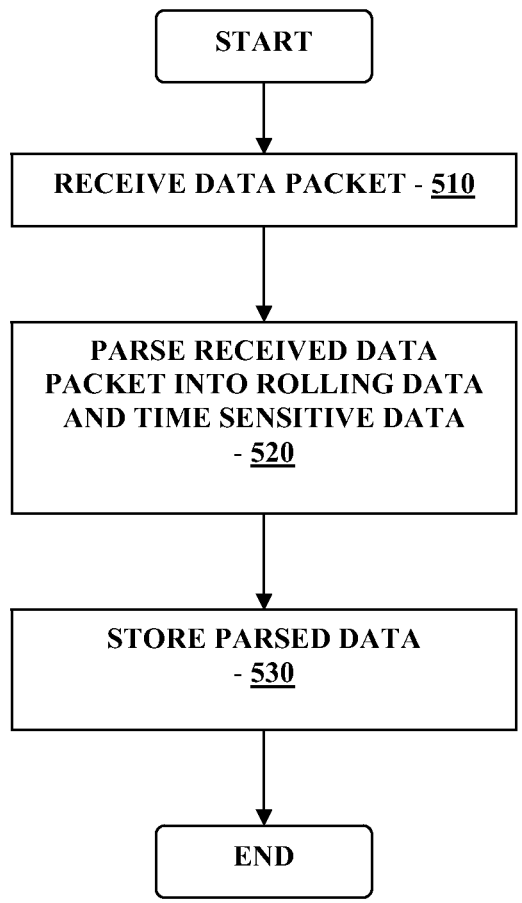
FIG. 5 is a flowchart illustrating data processing of the received data packet including the rolling data in accordance with one embodiment of the present disclosure.

FIG. 5 is a flowchart illustrating data processing of the received data packet including the rolling data in accordance with one embodiment of the present disclosure. Referring to FIG. 5, when the data packet is received (510) (for example, by one or more of the receivers 104, 106, in one embodiment) the received data packet is parsed so that the urgent data may be separated from the not-urgent data (stored in, for example, the rolling data field in the data packet) (520). Thereafter the parsed data is suitably stored in an appropriate memory or storage device (530).

In the manner described above, in accordance with one embodiment of the present disclosure, there is provided method and apparatus for separating non-urgent type data (for example, data associated with calibration) from urgent type data (for example, monitored analyte related data) to be transmitted over the communication link to minimize the potential burden or constraint on the available transmission time. More specifically, in one embodiment, non-urgent data may be separated from data that is required by the communication system to be transmitted immediately, and transmitted over the communication link together while maintaining a minimum transmission time window. In one embodiment, the non-urgent data may be parsed or broken up into a number of data segments, and transmitted over multiple data packets. The time sensitive immediate data (for example, the analyte sensor data, temperature data, etc.), may be transmitted over the communication link substantially in its entirety with each data packet or transmission.

Figure 6:
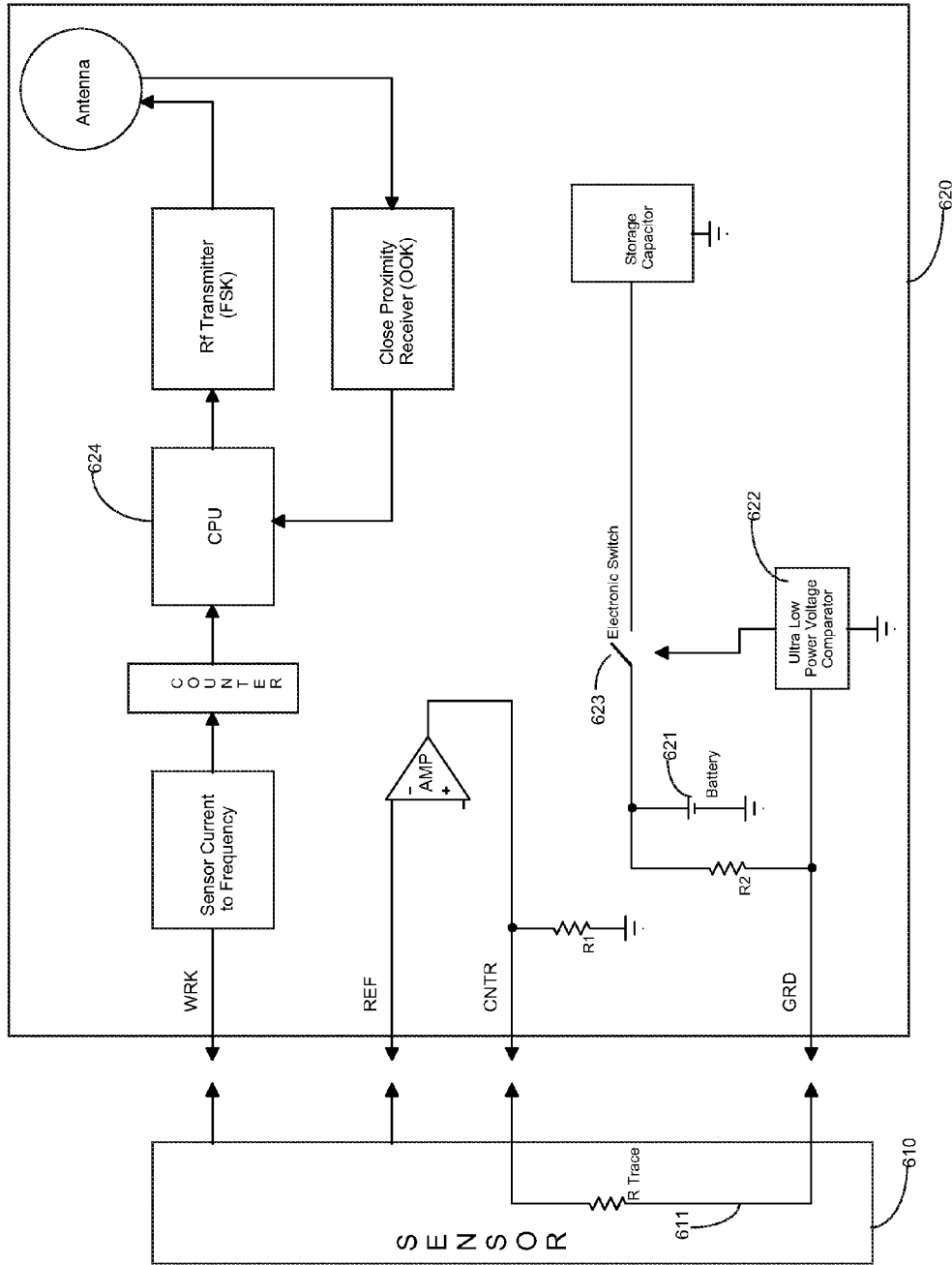
FIG. 6 is a block diagram illustrating the sensor unit and the transmitter unit of the data monitoring and management system of FIG. 1 in accordance with one embodiment of the present disclosure.

FIG. 6 is a block diagram illustrating the sensor unit and the transmitter unit of the data monitoring and management system of FIG. 1 in accordance with one embodiment of the present disclosure. Referring to FIG. 6, in one aspect, a transmitter unit 620 is provided in a substantially water tight and sealed housing. The transmitter unit 620 includes respective contacts (wrk, ref, cntr, and grd) for respectively establishing electrical contact with one or more of the working electrode, the reference electrode, the counter electrode and the ground terminal (or guard trace) of the sensor unit 610. Also shown in FIG. 6 is a conductivity bar/trace 611 provided on the sensor unit 610. For example, in one embodiment, the conductivity bar/trace 611 may comprise a carbon trace on a substrate layer of the sensor unit 610. In this manner, in one embodiment, when the sensor unit 610 is coupled to the transmitter unit 620, electrical contact is established, for example, via the conductivity bar/trace 611 between the contact pads or points of the transmitter unit 620 (for example, at the counter electrode contact (cntr) and the ground terminal contact (grd)) such that the transmitter unit 620 may be powered for data communication.

That is, during manufacturing of the transmitter unit 620, in one aspect, the transmitter unit 620 is configured to include a power supply such as battery 621. Further, during the initial non-use period (e.g., post manufacturing sleep mode), the transmitter unit 620 is configured such that it is not used and thus drained by the components of the transmitter unit 620. During the sleep mode, and prior to establishing electrical contact with the sensor unit 610 via the conductivity bar/trace 611, the transmitter unit 620 is provided with a low power signal from, for example, a low power voltage comparator 622, via an electronic switch 623 to maintain the low power state of, for example, the transmitter unit 620 components. Thereafter, upon connection with the sensor unit 610, and establishing electrical contact via the conductivity bar/trace 611, the embedded power supply 621 of the transmitter unit 620 is activated or powered up so that some or all of the components of the transmitter unit 620 are configured to receive the necessary power signals for operations related to, for example, data communication, processing and/or storage.

In one aspect, since the transmitter unit 620 is configured to a sealed housing without a separate replaceable battery compartment, in this manner, the power supply of the battery 621 is preserved during the post manufacturing sleep mode prior to use.

In a further aspect, the transmitter unit 620 may be disposed or positioned on a separate on-body mounting unit that may include, for example, an adhesive layer (on its bottom surface) to firmly retain the mounting unit on the skin of the user, and which is configured to receive or firmly position the transmitter unit 620 on the mounting unit during use. In one aspect, the mounting unit may be configured to at least partially retain the position of the sensor unit 610 in a transcutaneous manner so that at least a portion of the sensor unit is in fluid contact with the analyte of the user. Example embodiments of the mounting or base unit and its cooperation or coupling with the transmitter unit are provided, for example, in U.S. Pat. No. 6,175,752, incorporated herein by reference for all purposes.

In such a configuration, the power supply for the transmitter unit 620 may be provided within the housing of the mounting unit such that, the transmitter unit 620 may be configured to be powered on or activated upon placement of the transmitter unit 620 on the mounting unit and in electrical contact with the sensor unit 610. For example, the sensor unit 610 may be provided pre-configured or integrated with the mounting unit and the insertion device such that, the user may position the sensor unit 610 on the skin layer of the user using the insertion device coupled to the mounting unit. Thereafter, upon transcutaneous positioning of the sensor unit 610, the insertion device may be discarded or removed from the mounting unit, leaving behind the transcutaneously positioned sensor unit 610 and the mounting unit on the skin surface of the user.

Thereafter, when the transmitter unit 620 is positioned on, over or within the mounting unit, the battery or power supply provided within the mounting unit is configured to electrically couple to the transmitter unit 620 and/or the sensor unit 610. Given that the sensor unit 610 and the mounting unit are provided as replaceable components for replacement every 3, 5, 7 days or other predetermined time periods, the user is conveniently not burdened with verifying the status of the power supply providing power to the transmitter unit 620 during use. That is, with the power supply or battery replaced with each replacement of the sensor unit 610, a new power supply or battery will be provided with the new mounting unit for use with the transmitter unit 620.

Referring to FIG. 6 again, in one aspect, when the sensor unit 610 is removed from the transmitter unit 620 (or vice versa), the electrical contact is broken and the conductivity bar/trace 611 returns to an open circuit. In this case, the transmitter unit 620 may be configured, to detect such condition and generate a last gasp transmission sent to the primary receiver unit 104 (and/or the secondary receiver unit 106) indicating that the sensor unit 610 is disconnected from the transmitter unit 620, and that the transmitter unit 620 is entering a powered down (or low power off) state. And the transmitter unit 620 is powered down into the sleep mode since the connection to the power supply (that is embedded within the transmitter unit 620 housing) is broken.

In this manner, in one aspect, the processor 624 of the transmitter unit 620 may be configured to generate the appropriate one or more data or signals associated with the detection of sensor unit 610 disconnection for transmission to the receiver unit 104 (FIG. 1), and also, to initiate the power down procedure of the transmitter unit 620. In one aspect, the components of the transmitter unit 620 may be configured to include application specific integrated circuit (ASIC) design with one or more state machines and one or more nonvolatile and/or volatile memory units such as, for example, EEPROMs and the like.

Referring again to FIGS. 1 and 6, in one embodiment, the communication between the transmitter unit 620 (or 102 of FIG. 1) and the primary receiver unit 104 (and/or the secondary receiver unit 106) may be based on close proximity communication where bi-directional (or uni-directional) wireless communication is established when the devices are physically located in close proximity to each other. That is, in one embodiment, the transmitter unit 620 may be configured to receive very short range commands from the primary receiver unit 104 (FIG. 1) and perform one or more specific operations based on the received commands from the receiver unit 104.

In one embodiment, to maintain secure communication between the transmitter unit and the data receiver unit, the transmitter unit ASIC may be configured to generate a unique close proximity key at power on or initialization. In one aspect, the 4 or 8 bit key may be generated based on, for example, the transmitter unit identification information, and which may be used to prevent undesirable or unintended communication. In a further aspect, the close proximity key may be generated by the receiver unit based on, for example, the transmitter identification information received by the transmitter unit during the initial synchronization or pairing procedure of the transmitter and the receiver units.

Referring again to FIGS. 1 and 6, in one embodiment, the transmitter unit ASIC configuration may include a 32 KHz oscillator and a counter which may be configured to drive the state machine in the transmitter unit ASIC. The transmitter ASIC configuration may include a plurality of close proximity communication commands including, for example, new sensor initiation, pairing with the receiver unit, and RF communication control, among others. For example, when a new sensor unit is positioned and coupled to the transmitter unit so that the transmitter unit is powered on, the transmitter unit is configured to detect or receive a command from the receiver unit positioned in close proximity to the transmitter unit. For example, the receiver unit may be positioned within a couple of inches from the on-body position of the transmitter unit, and when the user activates or initiates a command associated with the new sensor initiation from the receiver unit, the transmitter unit is configured to receive the command from the receiver and, in its response data packet, transmit, among others, its identification information back to the receiver unit.

In one embodiment, the initial sensor unit initiation command does not require the use of the close proximity key. However, other predefined or preconfigured close-proximity commands may be configured to require the use of the 8 bit key (or a key of a different number of bits). For example, in one embodiment, the receiver unit may be configured to transmit an RF on/off command to turn on/off the RF communication module or unit in the transmitter unit 102. Such RF on/off command in one embodiment includes the close proximity key as part of the transmitted command for reception by the transmitter unit.

During the period that the RF communication module or unit is turned off based on the received close proximity command, the transmitter unit does not transmit any data, including any glucose related data. In one embodiment, the glucose related data from the sensor unit which is not transmitted by the transmitter unit during the time period when the RF communication module or unit of the transmitter unit is turned off may be stored in a memory or storage unit of the transmitter unit for subsequent transmission to the receiver unit when the transmitter unit RF communication module or unit is turned back on based on the RF-on command from the receiver unit. In this manner, in one embodiment, the transmitter unit may be powered down (temporarily, for example, during air travel) without removing the transmitter unit from the on-body position.

Figure 7:
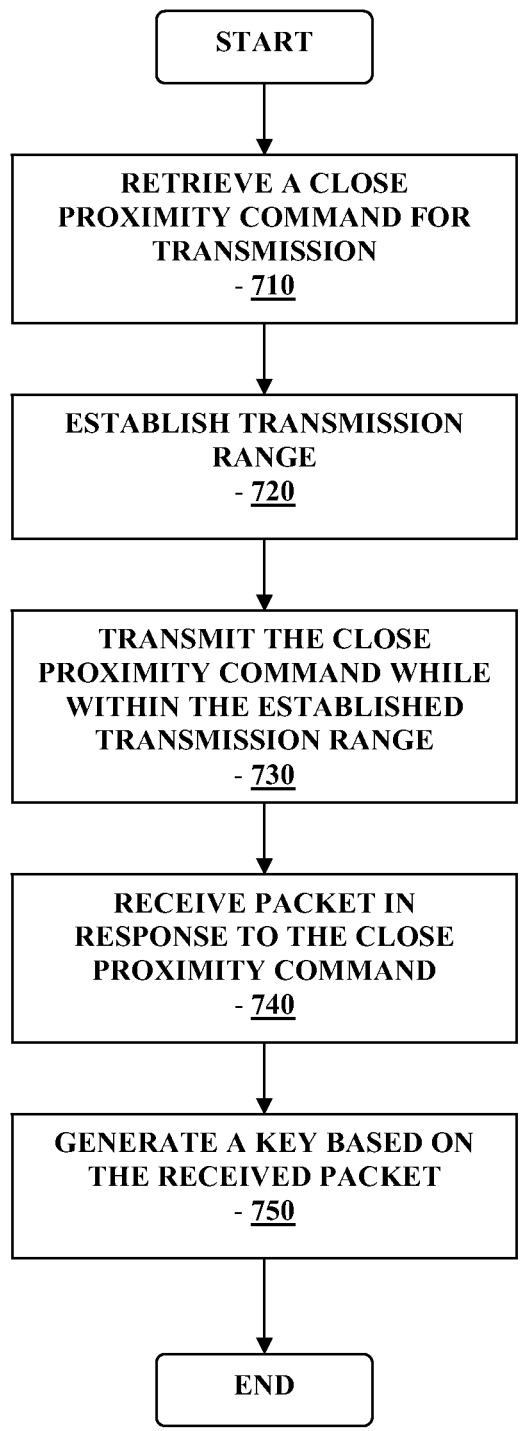
FIG. 7 is a flowchart illustrating data communication using close proximity commands in the data monitoring and management system of FIG. 1 in accordance with one embodiment of the present disclosure.

FIG. 7 is a flowchart illustrating data communication using close proximity commands in the data monitoring and management system of FIG. 1 in accordance with one embodiment of the present disclosure. Referring to FIG. 7, the primary receiver unit 104 (FIG. 1) in one aspect may be configured to retrieve or generate a close proximity command (710) for transmission to the transmitter unit 102. To establish the transmission range (720), the primary receiver unit 104 may be positioned physically close to (that is, within a predetermined distance from) the transmitter unit 102. For example, the transmission range for the close proximity communication may be established at approximately one foot distance or less between the transmitter unit 102 and the primary receiver unit 104. When the transmitter unit 102 and the primary receiver unit 104 are within the transmission range, the close proximity command, upon initiation from the receiver unit 104 may be transmitted to the transmitter unit 102 (730).

Referring back to FIG. 7, in response to the transmitted close proximity command, a response data packet or other responsive communication may be received (740). In one aspect, the response data packet or other responsive communication may include identification information of the transmitter unit 102 transmitting the response data packet or other response communication to the receiver unit 104. In one aspect, the receiver unit 104 may be configured to generate a key (for example, an 8 bit key or a key of a predetermined length) based on the transmitter identification information (750), and which may be used in subsequent close proximity communication between the transmitter unit 102 and the receiver unit 104.

In one aspect, the data communication including the generated key may allow the recipient of the data communication to recognize the sender of the data communication and confirm that the sender of the data communication is the intended data sending device, and thus, including data which is desired or anticipated by the recipient of the data communication. In this manner, in one embodiment, one or more close proximity commands may be configured to include the generated key as part of the transmitted data packet. Moreover, the generated key may be based on the transmitter ID or other suitable unique information so that the receiver unit 104 may use such information for purposes of generating the unique key for the bi-directional communication between the devices.

While the description above includes generating the key based on the transmitter unit 102 identification information, within the scope of the present disclosure, the key may be generated based on one or more other information associated with the transmitter unit 102, and/or the receiver unit combination. In a further embodiment, the key may be encrypted and stored in a memory unit or storage device in the transmitter unit 102 for transmission to the receiver unit 104.

Figure 8:
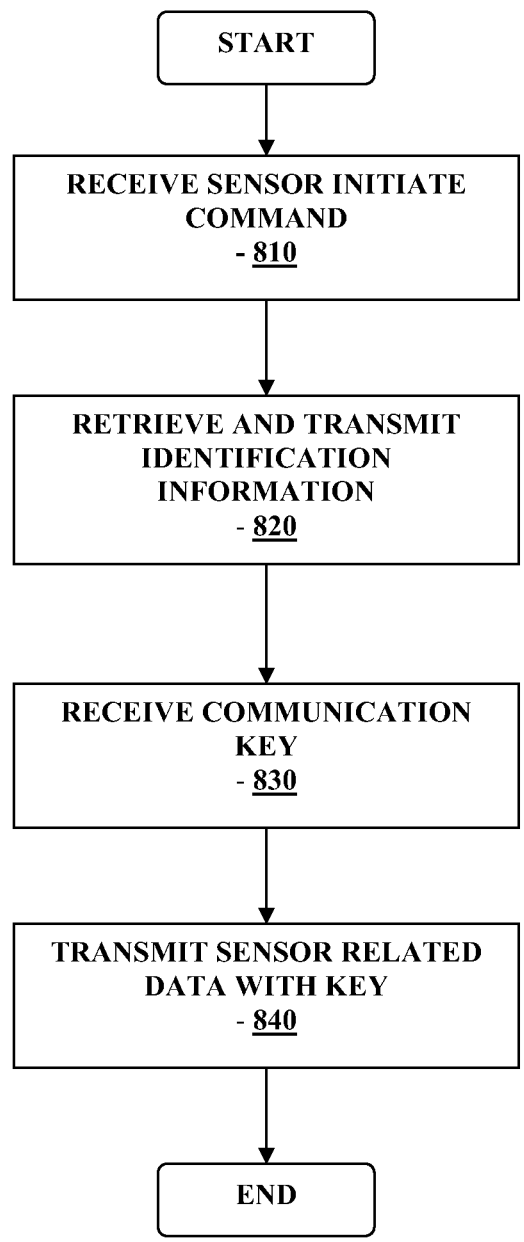
FIG. 8 is a flowchart illustrating the pairing or synchronization routine in the data monitoring and management system of FIG. 1 in accordance with one embodiment of the present disclosure.

FIG. 8 is a flowchart illustrating the pairing or synchronization routine in the data monitoring and management system of FIG. 1 in accordance with one embodiment of the present disclosure. Referring to FIG. 8, in one embodiment, the transmitter unit 102 may be configured to receive a sensor initiate close proximity command (810) from the receiver unit 104 positioned within the close transmission range. Based on the received sensor initiate command, the transmitter unit identification information may be retrieved (for example, from a nonvolatile memory) and transmitted (820) to the receiver unit 104 or the sender of the sensor initiate command.

Referring back to FIG. 8, a communication key (830) optionally encrypted is received in one embodiment, and thereafter, sensor related data is transmitted with the communication key on a periodic basis such as, every 60 seconds, five minutes, or any suitable predetermined time intervals (840).

Figure 9:
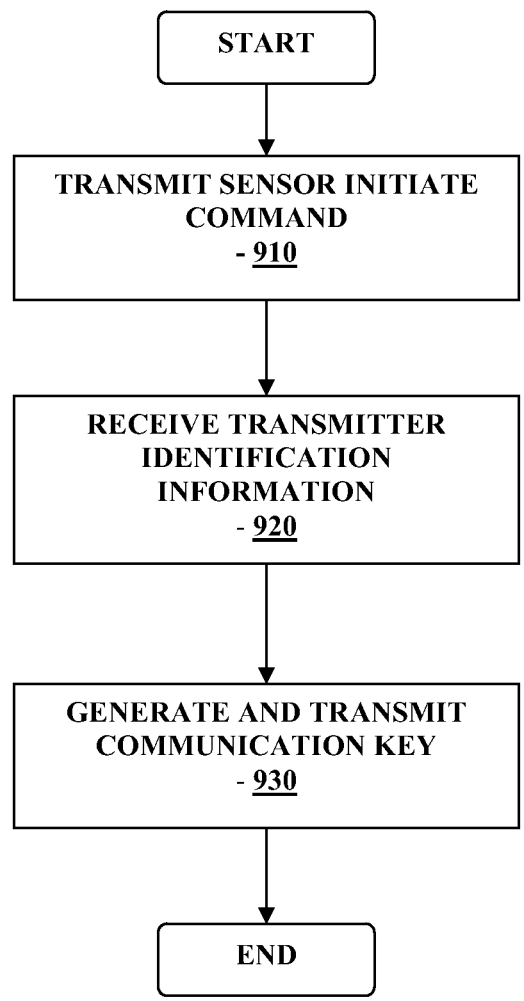
FIG. 9 is a flowchart illustrating the pairing or synchronization routine in the data monitoring and management system of FIG. 1 in accordance with another embodiment of the present disclosure.

Referring now to FIG. 9, a flowchart illustrating the pairing or synchronization routine in the data monitoring and management system of FIG. 1 in accordance with another embodiment of the present disclosure is shown. That is, in one aspect, FIG. 9 illustrates the pairing or synchronization routine from the receiver unit 104. Referring back to FIG. 9, the sensor initiate command is transmitted to the transmitter unit 102 (910) when the receiver unit 104 is positioned within a close transmission range. Thereafter, in one aspect, the transmitter identification information is received (920) for example, from the transmitter unit that received the sensor initiate command. Thereafter, a communication key (optionally encrypted) may be generated and transmitted (930) to the transmitter unit.

In the manner described above, in one embodiment, a simplified pairing or synchronization between the transmitter unit 102 and the receiver unit 104 may be established using, for example, close proximity commands between the devices. As described above, in one aspect, upon pairing or synchronization, the transmitter unit 102 may be configured to periodically transmit analyte level information to the receiver unit for further processing.

Figure 10:
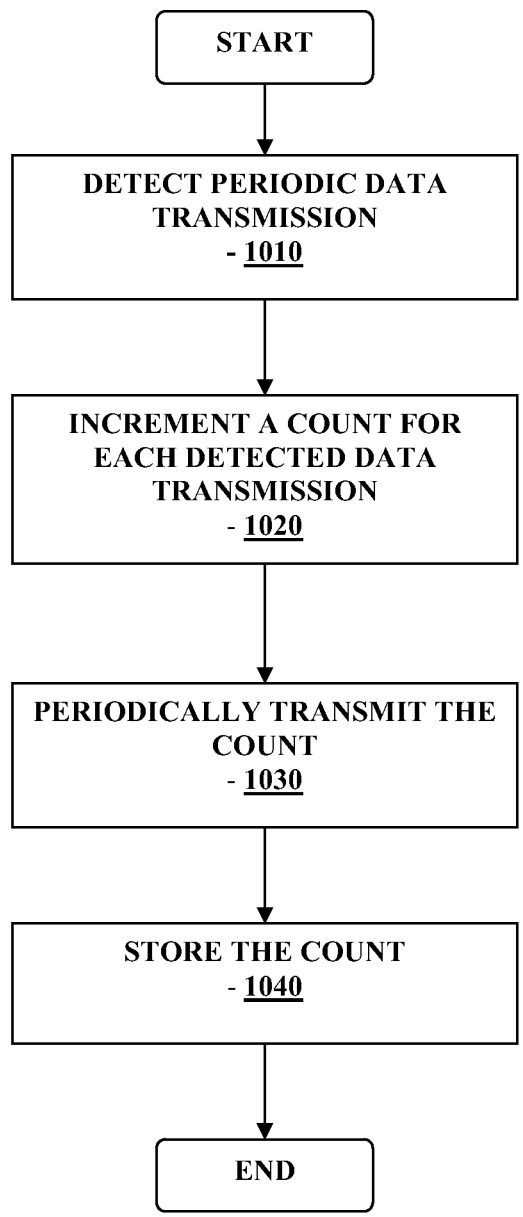
FIG. 10 is a flowchart illustrating the power supply determination in the data monitoring and management system of FIG. 1 in accordance with one embodiment of the present disclosure.

FIG. 10 is a flowchart illustrating the power supply determination in the data monitoring and management system of FIG. 1 in accordance with one embodiment of the present disclosure. That is, in one embodiment, using a counter, the receiver unit 104 may be configured to determine the power supply level of the transmitter unit 102 battery so as to determine a suitable time for replacement of the power supply or the transmitter unit 102 itself. Referring to FIG. 10, periodic data transmission is detected (1010), and a corresponding count in the counter is incremented for example, by one with each detected data transmission (1020). In particular, a Hobbs counter may be used in the rolling data configuration described above to provide a count that is associated with the transmitter unit data transmission occurrence.

Referring to FIG. 10, the updated or incremented count stored in the Hobbs counter is periodically transmitted in the data packet from the transmitter unit 102 to the receiver unit 104 (1030). Moreover, the incremented or updated count may be stored (1040) in a persistent nonvolatile memory unit of the transmitter unit 102. Accordingly, based on the number of data transmission occurrences, the battery power supply level may be estimated, and in turn, which may provide an indication as to when the battery (and thus the transmitter unit in the embodiment where the power supply is manufactured to be embedded within the transmitter unit housing) needs to be replaced.

Moreover, in one aspect, the incremented count in the Hobbs counter is stored in a persistent nonvolatile memory such that, the counter is not reset or otherwise restarted with each sensor unit replacement.

Figure 11:
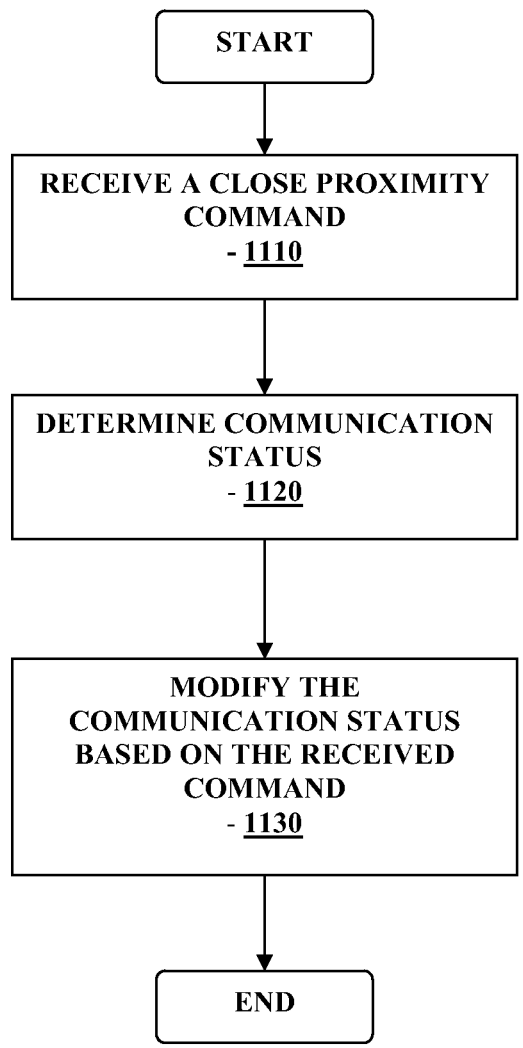
FIG. 11 is a flowchart illustrating close proximity command for RF communication control in the data monitoring and management system of FIG. 1 in accordance with one embodiment of the present disclosure.

FIG. 11 is a flowchart illustrating close proximity command for RF communication control in the data monitoring and management system of FIG. 1 in accordance with one embodiment of the present disclosure. Referring to FIG. 11, a close proximity command associated with communication status, for example is received (1110). In one aspect, the command associated with the communication status may include, for example, a communication module turn on or turn off command for, for example, turning on or turning off the associated RF communication device of the transmitter unit 102. Referring to FIG. 11, the communication status is determined (1120), and thereafter, modified based on the received command (1130).

That is, in one aspect, using one or more close proximity commands, the receiver unit 104 may be configured to control the RF communication of the transmitter unit 102 to, for example, disable or turn off the RF communication functionality for a predetermined time period. This may be particularly useful when used in air travel or other locations such as hospital settings, where RF communication devices need to be disabled. In one aspect, the close proximity command may be used to either turn on or turn off the RF communication module of the transmitter unit 102, such that, when the receiver unit 104 is positioned in close proximity to the transmitter unit 102, and the RF command is transmitted, the transmitter unit 102 is configured, in one embodiment, to either turn off or turn on the RF communication capability of the transmitter unit 102.

Figure 12:
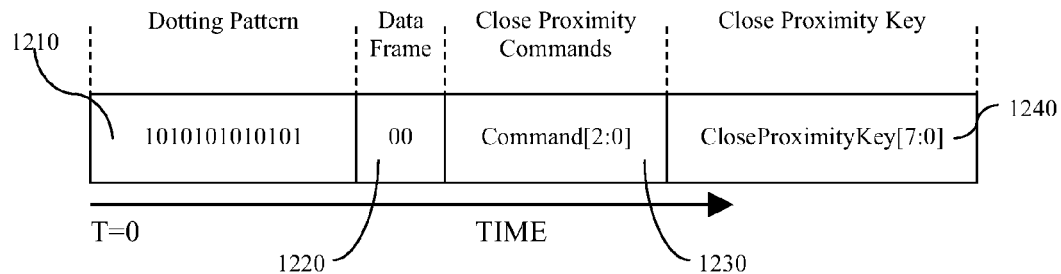
FIG. 12 illustrates a data format of a close proximity data packet sent by a controller, for use in one or more embodiments of the present disclosure.

FIG. 12 illustrates a data format of a close proximity data packet sent by a controller such as the receiver unit 104/106 to the transmitter unit 620 (FIG. 6) in the analyte monitoring system 100 (FIG. 1). Referring to FIG. 12, in one embodiment, a close proximity data packet sent by the controller may include 24 bits of data. In one aspect, the 24 bit data packet may include a dotting pattern 1210, a data frame 1220, one or more close proximity commands 1230, and a close proximity key 1240. As discussed in further detail below, in one embodiment, a sequence detector 1330 (FIG. 13) in the transmitter unit 620 ASIC logic uses the dotting pattern 1210 and the data frame 1220 to determine whether the incoming data is a proper close proximity data packet. In one aspect, the close proximity data packet as shown in FIG. 12 may include dotting pattern 1210 which may be used by the close proximity detector logic to detect and synchronize the received data, the data frame 1220 that includes bit pattern prior to the actual received data, the close proximity commands 1230, and close proximity key 1240 to validate the close proximity communication.

In one aspect, there may be five valid close proximity commands 1230 and the close proximity key 1240 may be used as a validation for the communication received from the controller (receiver unit 104/106) for example. While a 24 bit data packet for the close proximity command and five valid close proximity commands 1230 are described above, within the scope of the present disclosure, the data packet for the close proximity commands may include greater or less number of bits within the data packet, and further, the number of valid close proximity commands may be greater or fewer than five valid close proximity commands as described above.

Figure 13:
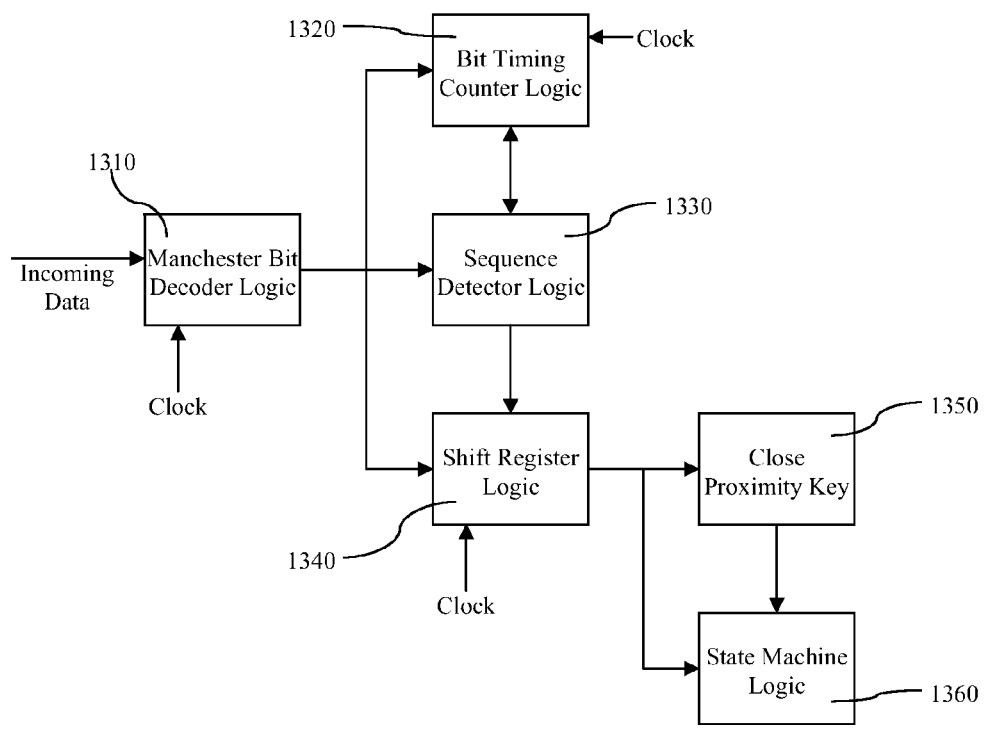
FIG. 13 is a block diagram representation of a close proximity detection logic of the transmitter unit 620 in one or more embodiments of the present disclosure.

FIG. 13 is a block diagram representation of a close proximity detection logic of the transmitter unit 620 in one or more embodiments of the present disclosure. Referring to FIG. 13, in one embodiment, incoming Manchester encoded data packet, for example, from the controller (receiver unit 104/106) is received at a rate of approximately 4.8 Kbits/second by the close proximity detector logic and decoded by a Manchester bit decoder logic 1310. The Manchester bit decoder logic 1310 detects the two data symbols and may be configured to convert the detected data to one data bit at 2.4 Kbits/sec.

In one aspect, the decoded data bit is sent to a bit timing counter logic 1320, a sequence detector logic 1330, and the shift register logic 1340. In one embodiment, the sequence detector logic 1330 looks for a predetermined data pattern showing the authenticity of the received data packet. In one aspect, the predetermined data pattern, for example '0100', includes an occurrence of a dotting pattern '01' and a data frame '00'. If only a partial sequence is detected followed by an incorrect data bit, the sequence detector logic 1330 may be configured to reset and wait for the next data packet. On the other hand, if the correct data packet is received with the expected or anticipated predetermined data pattern, for example, a '0100', then the sequence detector logic 1330 deems the data packet to be valid.

When the data packet is determined to have the correct dotting pattern and data frame, and is deemed to be valid, a reset signal is disabled and a shift register signal is enabled. With a shift register signal enabled, each incoming bit of validated data is latched into an 11 bit envelope detector shift register logic 1340. Once the 11$^{th}$ bit is latched into the register 1340, an on/off keying (OOK) signal indicates that close proximity communication has been completed. Once a close proximity command is sent and decoded, an envelope detect finite state machine (FSM) logic 1360 is configured to process the command. During the processing period, no further commands are accepted, and the close proximity state machine logic 1360 is locked in a final state. Once the command has been processed, the close proximity logic is reset by a logic reset signal. The close proximity logic then returns to its initial state and awaits further instructions.

Referring again to FIG. 13, a close proximity key 1350 may be used in conjunction with the close proximity command data packet to determine or confirm the identity of the close proximity command issuing device, such as, for example, the controller (receiver unit 104/106). For example, in one aspect, each transmitter unit 102, 620 (FIGS. 1, 6) may have a unique key based on, for example, the device serial or identification number. This value may be latched or stored, and provided to the close proximity logic, and when a close proximity communication is completed, the received key value as part of the close proximity command data packet is compared to the latched unique key. If the two values match, a signal corresponding to a key match is set high, indicating that the close proximity command received is intended for the transmitter unit that received the command.

Referring again to FIG. 13, a time out signal in conjunction with a bit timing counter 1320 may be used to determine whether transmission errors may have occurred. For example, each time a valid data bit is received by the close proximity logic of the transmitter unit 102/620, a time out signal is generated by the bit timing counter logic 1320. In one aspect, the time period between each time out signal is compared by the bit timing counter logic 1320, and if it is determined that the time period is greater than a predetermined time period based on the data bit time (for example, approximately 1.75 times the data bit time), then it is determined that the data transmission is in error. If it is determined that the transmission is in error, the state machine logic 1360 may be configured to reset the shift register logic 1340, sequence detector logic 1330, and the bit timer logic 1320. On the other hand, when it is determined that the data transmission is not in error, that is, when the time period between each time out signal compared by the bit timing counter logic 1320 is below the predetermined time period, then the data bit associated with the current data communication is considered valid.

Referring still to FIG. 13, a clock signal is provided to the Manchester bit decoder logic 1310, the bit timing counter logic 1320 and the shift register logic 1340 to, among others, synchronize the operation of the various routines executed by the components of the close proximity detector logic in the transmitter unit of the analyte monitoring system. Additionally, in the manner described, the close proximity detector logic may be configured to use small logic blocks running at a relatively slower clock rate, resulting in, for example, reduction in the required ASIC resources and/or power consumption. Furthermore, the embodiments of the close proximity detector logic described above provides a standalone continuous OOK detection without the use of a microcontroller that requires relatively more power and ASIC resources (for example, ASIC area).

Indeed, in accordance with embodiments of the present disclosure, the transmitted OOK data packets from the receiver unit (104/106) may be decoded in conjunction with the received close proximity commands using, for example, one or more of a Manchester decode block logic, error detection logics and a command decoder logic. Furthermore, while Manchester decoder logic is described above, within the scope of the present disclosure, other data encoding/decoding techniques may be used, for example, other binary phase-shift keying (BPSK).

Figure 14:
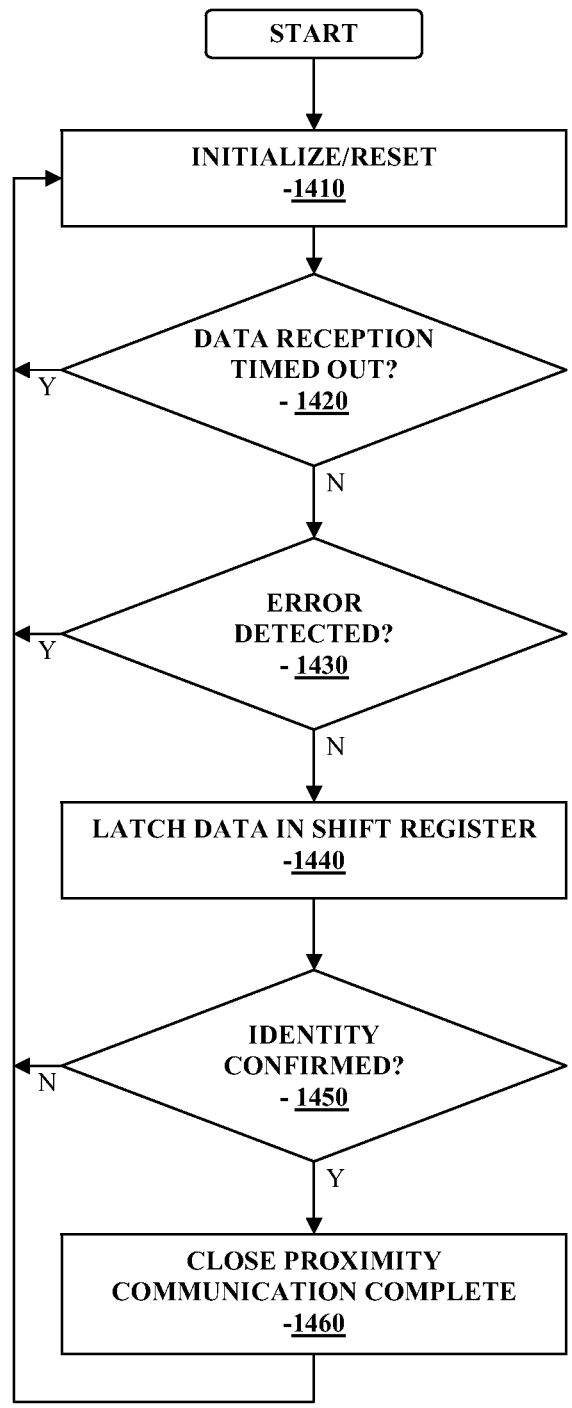
FIG. 14 is a flow chart illustrating close proximity detection logic in one or more embodiments of the present disclosure.

FIG. 14 is a flow chart illustrating close proximity detection logic in one or more embodiments of the present disclosure. Referring to FIGS. 13 and 14, when a close proximity communication mode is activated in a data communication system for example, in the analyte monitoring system 100 (FIG. 1), the close proximity detector logic may be configured to continuously monitor to detect an incoming command or data signal. When the close proximity logic activated, an initial initialization occurs (1410) to clear data bits to ensure no incorrect signals are sent to the close proximity logic. The close proximity detector logic waits to receive one or more data packet (1420). As discussed above, the Manchester encoded data packets may be received at a rate of 4.8 Kbits/sec. When data is not received, the logic may time out and return to the initialization state (1410).

On the other hand, when the data packet is received, error correction is performed to determine the validity of the received data packet (1430). For example, as discussed above, the sequence detection logic may be configured to analyze the dotting pattern and the data frame of the received data packet to determine whether the data packet is valid. If it is determined that the analyzed dotting pattern and the data frame results in the detection of a particular sequence in the data pattern, then in one aspect, the routine may return to the reset/initialization state (1410). However, when it is determined that the received data packet is valid, the data packet is latched (1440), for example, in the shift register as discussed above. Indeed, when the 11$^{th}$ bit in the data packet is received, in one aspect, it is determined that the close proximity communication is completed (1460).

Referring to FIGS. 13 and 14, the close proximity key is compared to confirm that the command received is intended for the transmitter device receiving the command (1450). For example, as discussed above in conjunction with FIG. 13, the data packet received may include a unique transmitter identification information (such as a serial number or other unique information). This information may be compared with a stored value to determine whether the information received matches the value stored. If it is determined that the close proximity key does not match, in one aspect, the routine returns to the initialization/reset state (1410), as the received data packet is not intended for the device that received the packet. On the other hand, if the closed proximity key matches the stored information or unique value, in one aspect, the state machine logic may be configured to generate the OOK signal confirming the receipt of the valid close proximity communication, and the state machine logic may be configured to perform the requested function or execute the one or more routines associated with the received close proximity command.

In this manner, embodiments of the present disclosure provide method and apparatus for optimizing power consumption and ASIC resources in communication devices such as transmitter unit 620 of the analyte monitoring system described above, or on-body patch pump for infusing medication such as insulin, or other therapeutic agents.

It is to be noted that while exemplary embodiments described above include configurations that have specific data packet size, transmission rate, size of the shift register, error correction techniques, and the like, within the scope of the present disclosure, other suitable variations are fully contemplated.

A method in one aspect includes receiving an encoded data packet including one or more error detection bits, one or more close proximity commands, and a communication identifier, decoding the received data packet, performing error detection based on the one or more error detection bits, validating the decoded received data packet, and executing one or more routines associated with the respective one or more close proximity commands when the decoded received data packet is validated, where the executed one or more routines includes transmitting analyte related data.

The received data packet may be Manchester encoded.

The one or more error detection bits may include a predetermined bit pattern such as a dotting pattern, for example.

In a further aspect, decoding the received data packet may include performing Manchester decoding.

Also, validating the decoded received data packet may include comparing the received communication identifier in the data packet with a stored value.

The communication identifier may include a device identification information.

The one or more routines may be associated with the operation of an analyte monitoring device.

The executed one or more routines may include a power on routine, a power off routine, data transfer initiation routine, or data transfer disable routine.

The analyte related data may include a monitored analyte level, such as glucose level.

In a further aspect, the method may include storing the received data packet.

A method in accordance with another embodiment includes receiving an encoded data packet including a close proximity command and a communication identifier, decoding the received data packet, validating the decoded received data packet, and executing one or more routines associated with the respective one or more close proximity commands when the decoded received data packet is validated.

In one aspect, validating the decoded received data packet may include comparing the received communication identifier in the data packet with a stored value.

Further, validating the decoded received data packet may include performing error detection on the data packet, including, for example, comparing one or more data pattern in the received data packet.

The communication identifier may include a device identification information.

The one or more routines may be associated with the operation of an analyte monitoring device.

The executed one or more routines may include a power on routine, a power off routine, data transfer initiation routine, or data transfer disable routine.

In still another aspect, the method may include receiving a signal associated with an analyte level, where the analyte includes glucose.

Also, the decoded received data packet may be stored in, for example, a memory, storage device, or the like.

An apparatus in accordance with still another embodiment includes a communication interface, one or more processors coupled to the communication interface, and a memory for storing instructions which, when executed by the one or more processors, causes the one or more processors to receive an encoded data packet including one or more error detection bits, one or more close proximity commands, and a communication identifier over the communication interface, decode the received data packet, perform error detection based on the one or more error detection bits, validate the decoded received data packet, and execute one or more routines associated with the respective one or more close proximity commands when the decoded received data packet is validated, wherein the executed one or more routines includes transmitting analyte related data.

The memory for storing instructions which, when executed by the one or more processors, may cause the one or more processors to Manchester decode the received data packet.

The one or more error detection bits may include a predetermined bit pattern including, for example, a dotting pattern.

The memory for storing instructions which, when executed by the one or more processors, may cause the one or more processors to Manchester decode the received data packet.

The memory for storing instructions which, when executed by the one or more processors, may cause the one or more processors to compare the received communication identifier in the data packet with a stored value to validate the received data packet.

The memory for storing instructions which, when executed by the one or more processors, may cause the one or more processors to store the received data packet in the memory.

The one or more processors may include an application specific integrated circuit (ASIC).

In the manner described, in accordance with embodiments of the present disclosure, the close proximity detector logic may be configured to use small logic blocks running at a relatively slower clock rate, resulting in, for example, reduction in the required ASIC area and power consumption. Furthermore, the embodiments of the close proximity detector logic described above provides a standalone continuous OOK detection without the use of a microcontroller that requires relatively more power and ASIC resources.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present disclosure and that structures and methods within the scope of these claims and their equivalents be covered thereby.

What is claimed is:

1. A method, comprising:
   establishing a communication range between a data processing unit and a control unit by placing the control unit within a predetermined distance from the data processing unit;
   receiving an encoded data packet at the data processing unit when the control unit is within the predetermined distance, wherein the received encoded data packet includes one or more activation commands and a communication identifier;
   decoding the received data packet;
   validating the decoded received data packet; and
   executing one or more routines associated with the one or more activation commands configured to control a communication or processing of analyte related data;
   wherein the executed one or more routines includes activating the data processing unit to communicate the analyte related data.

2. The method of claim 1 including executing the one or more routines associated with the one or more activation commands when the decoded received data packet is validated.

3. The method of claim 1 wherein validating the decoded received data packet includes comparing the communication identifier in the decoded received data packet with a stored value.

4. The method of claim 1 wherein validating the decoded received data packet includes performing error detection on the decoded received data packet.

5. The method of claim 4 wherein performing error detection on the data packet includes comparing one or more data patterns in the decoded received data packet.

6. The method of claim 4 wherein performing error detection on the data packet includes performing error detection based on one or more error detection bits.

7. The method of claim 6 wherein the received encoded data packet includes the one or more error detection bits.

8. The method of claim 6 wherein the one or more error detection bits includes a predetermined bit pattern.

9. The method of claim 8 wherein the predetermined bit pattern includes a dotting pattern.

10. The method of claim 1 wherein the encoded data packet is Manchester encoded.

11. The method of claim 10 wherein decoding the received data packet includes performing Manchester decoding.

12. The method of claim 1 wherein the communication identifier includes a device identification information.

13. The method of claim 1 wherein the one or more routines are associated with an operation of an analyte monitoring device.

14. The method of claim 1 wherein the one or more routines includes a power on routine, a power off routine, a data transfer initiation routine, or a data transfer disable routine.

15. The method of claim 1 including receiving a signal associated with an analyte level.

16. The method of claim 15 wherein the analyte level is a glucose level.

17. The method of claim 1 including storing the decoded received data packet.

18. The method of claim 3 wherein the one or more routines includes determining a communication status of the data processing unit and modifying the communication status based on the one or more activation commands.

19. An apparatus, comprising:
    a communication interface;
    one or more processors coupled to the communication interface; and
    a memory for storing instructions which, when executed by the one or more processors, causes the one or more processors to establish a communication range between a data processing unit and a control unit by placing the control unit within a predetermined distance from the data processing unit, receive an encoded data packet at the data processing unit when the control unit is within the predetermined distance, wherein the received encoded data packet includes one or more activation commands and a communication identifier, decode the received data packet, validate the decoded received data packet, and execute one or more routines associated with the one or more activation commands configured to control a communication or processing of analyte related data, wherein the executed one or more routines includes activating the data processing unit to communicate the analyte related data.

20. The apparatus of claim 19 wherein the memory for storing instructions which, when executed by the one or more processors, causes the one or more processors to execute the one or more routines associated with the one or more activation commands when the decoded received data packet is validated.

21. The apparatus of claim 19 wherein the memory for storing instructions which, when executed by the one or more processors, causes the one or more processors to validate the decoded received data packet by comparing the communication identifier in the decoded received data packet with a stored value.

22. The apparatus of claim 19 wherein the memory for storing instructions which, when executed by the one or more processors, causes the one or more processors to compare the communication identifier in the decoded received data packet with a stored value.

23. The apparatus of claim 19 wherein the memory for storing instructions which, when executed by the one or more processors, causes the one or more processors to perform error detection on the decoded received data packet.

24. The apparatus of claim 23 wherein the memory for storing instructions which, when executed by the one or more processors, causes the one or more processors to perform error detection by comparing one or more data patterns in the decoded received data packet.

25. The apparatus of claim 23 wherein the memory for storing instructions which, when executed by the one or more processors, causes the one or more processors to perform error detection based on one or more error detection bits.

26. The apparatus of claim 25 wherein the received encoded data packet includes the one or more error detection bits.

27. The apparatus of claim 26 wherein the one or more error detection bits includes a predetermined bit pattern.

28. The apparatus of claim 27 wherein the predetermined bit pattern includes a dotting pattern.

29. The apparatus of claim 19 wherein the received data packet is Manchester encoded.

30. The apparatus of claim 29 wherein the memory for storing instructions which, when executed by the one or more processors, causes the one or more processors to Manchester decode the received data packet.

31. The apparatus of claim 19 wherein the memory for storing instructions which, when executed by the one or more processors, causes the one or more processors to Manchester decode the received data packet.

32. The apparatus of claim 19 wherein the communication identifier includes a device identification information.

33. The apparatus of claim 19 wherein the one or more routines includes a power on routine, a power off routine, a data transfer initiation routine, or a data transfer disable routine.

34. The apparatus of claim 19 wherein the analyte related data includes a monitored analyte level.

35. The apparatus of claim 34 wherein the analyte related data is glucose related data.

36. The apparatus of claim 19 wherein the memory for storing instructions which, when executed by the one or more processors, causes the one or more processors to store the received data packet in the memory.

37. The apparatus of claim 19 wherein the one or more processors include an application specific integrated circuit (ASIC).

38. The apparatus of claim 20 wherein the one or more routines includes determining a communication status of the data processing unit and modifying the communication status based on the one or more activation commands.

* * * * *